US007666581B2

(12) United States Patent
Srivastava

(10) Patent No.: US 7,666,581 B2
(45) Date of Patent: Feb. 23, 2010

(54) METHODS FOR PREPARING COMPOSITIONS COMPRISING HEAT SHOCK PROTEINS USEFUL FOR THE TREATMENT OF CANCER AND INFECTIOUS DISEASE

(75) Inventor: Pramod K. Srivastava, Avon, CT (US)

(73) Assignee: University of Connecticut Health Center, Farmington, CT (US)

( * ) Notice: Subject to any disclaimer, the term of this patent is extended or adjusted under 35 U.S.C. 154(b) by 33 days.

(21) Appl. No.: 10/225,367

(22) Filed: Aug. 20, 2002

(65) Prior Publication Data

US 2003/0129196 A1    Jul. 10, 2003

Related U.S. Application Data

(60) Provisional application No. 60/313,629, filed on Aug. 20, 2001, provisional application No. 60/337,222, filed on Dec. 6, 2001.

(51) Int. Cl.
    C12P 21/04    (2006.01)
(52) U.S. Cl. .................... 435/4; 435/69.7; 530/412
(58) Field of Classification Search .......... 530/412, 530/403
    See application file for complete search history.

(56) References Cited

U.S. PATENT DOCUMENTS

| | | | |
|---|---|---|---|
| 4,690,915 A | 9/1987 | Rosenberg | |
| 5,188,964 A | 2/1993 | McGuire et al. | |
| 5,232,833 A | 8/1993 | Sanders et al. | |
| 5,348,945 A | 9/1994 | Berberian et al. | |
| 5,580,859 A | 12/1996 | Felgner et al. | |
| 5,652,115 A | 7/1997 | Marks et al. | |
| 5,736,146 A | 4/1998 | Cohen et al. | |
| 5,747,332 A * | 5/1998 | Wallen et al. | ............... 435/272 |
| 5,750,119 A | 5/1998 | Srivastava | |
| 5,830,464 A | 11/1998 | Srivastava | |
| 5,837,251 A * | 11/1998 | Srivastava | ............... 424/193.1 |
| 5,856,201 A * | 1/1999 | Shoseyov et al. | ............ 436/501 |
| 5,869,058 A | 2/1999 | Cohen | |
| 5,891,653 A | 4/1999 | Attfield | |
| 5,935,576 A | 8/1999 | Srivastava | |
| 5,947,646 A | 9/1999 | Lytle | |
| 5,948,646 A | 9/1999 | Srivastava et al. | |
| 5,961,979 A | 10/1999 | Srivastava | |
| 5,985,270 A | 11/1999 | Srivastava | |
| 5,997,873 A | 12/1999 | Srivastava | |
| 6,017,540 A | 1/2000 | Srivastava | |
| 6,030,618 A | 2/2000 | Srivastava | |
| 6,048,530 A | 4/2000 | Srivastava | |
| 6,136,315 A | 10/2000 | Srivastava | |
| 6,162,436 A | 12/2000 | Srivastava | |
| 6,168,793 B1 | 1/2001 | Srivastava et al. | |
| 6,187,312 B1 | 2/2001 | Srivastava | |
| 6,312,711 B1 | 11/2001 | Duchateau et al. | ............... 435/7.1 |
| 6,338,945 B1 * | 1/2002 | Nicolette | ............... 435/7.1 |
| 6,399,070 B1 * | 6/2002 | Srivastava et al. | ........ 424/193.1 |
| 6,403,092 B1 | 6/2002 | Pizzo et al. | |
| 6,433,141 B1 | 8/2002 | Wallen et al. | |
| 6,689,363 B1 * | 2/2004 | Sette et al. | ............... 424/189.1 |
| 6,709,672 B2 | 3/2004 | Henot et al. | |
| 6,713,608 B2 | 3/2004 | Wallen et al. | |
| 6,730,302 B1 | 5/2004 | Fujihara et al. | |
| 6,797,480 B1 | 9/2004 | Srivastava | |
| 2002/0028207 A1 | 3/2002 | Srivastava | |
| 2002/0037290 A1 * | 3/2002 | Armen | ............... 424/178.1 |
| 2002/0172682 A1 | 11/2002 | Srivastava | |
| 2002/0192230 A1 | 12/2002 | Srivastava | |
| 2003/0211971 A1 | 11/2003 | Srivastava | |
| 2004/0253228 A1 | 12/2004 | Srivastava | |

FOREIGN PATENT DOCUMENTS

| | | |
|---|---|---|
| DE | 196 02 985 A1 | 1/1996 |
| GB | 2 251 186 A | 7/1992 |
| WO | WO 89/12455 | 12/1989 |
| WO | WO 90/02564 | 3/1990 |
| WO | WO 91/15572 | 10/1991 |
| WO | WO 92/01717 | 2/1992 |

(Continued)

OTHER PUBLICATIONS

Deutscher et al., Guide to protein purification, Method in enzymology, vol. 182.*
Xiao et al., (Archives of Biochemistry and biophysics, vol. 320, p. 96-105, 1995).*
Ojcius et al., J of Immunology, vol. 152, p. 2798-2810, 1994.*
Mazzoni et al., JBC, vol. 266, p. 14072-14081, 1991.*
Elliott Shaw Method of Enzymology, vol. 25, p. 655-660, 1972.*
Bartlett, 1972 "Effect Of Host Immunity On The Antigenic Strength Of Primary Tumors." *J. Natl. Cancer Inst.* 49:493-504.
Beverly, 1988, "Tumour Immunology." In: *Immunology*, 3rd Edition, Roitt, Ed., Mosby, London, pp. 17.1-17.12.

(Continued)

*Primary Examiner*—Larry R. Helms
*Assistant Examiner*—Lei Yao
(74) *Attorney, Agent, or Firm*—Jones Day

(57) ABSTRACT

The present invention relates to methods and compositions for the prevention and treatment of infectious diseases, and cancers. The methods of the invention comprises complexing a population of antigenic proteins or antigenic peptides derived from antigenic cells or viral particles to one or more different heat shock proteins in vitro. The population or the protein preparation used to produce the antigenic peptides comprises at least 50% of the different proteins or at least 50 different proteins of the antigenic cells or viral particles. Methods for making antigenic peptides comprise digesting a protein preparation of antigenic cells, a cellular fraction thereof, or of viral particles with one or more proteases, or exposing the protein preparation to ATP, guanidium hydrochloride, and/or acidic conditions.

46 Claims, No Drawings

FOREIGN PATENT DOCUMENTS

| | | |
|---|---|---|
| WO | WO 92/08484 | 5/1992 |
| WO | WO 92/08488 | 5/1992 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/18150 | 9/1993 |
| WO | WO 93/21529 | 10/1993 |
| WO | WO 93/24136 | 12/1993 |
| WO | WO 94/03208 | 2/1994 |
| WO | WO 94/04676 | 3/1994 |
| WO | WO 94/11513 | 5/1994 |
| WO | WO 94/14976 | 7/1994 |
| WO | WO94/14976 * | 7/1994 |
| WO | WO 94/29459 | 12/1994 |
| WO | WO 95/24923 | 9/1995 |
| WO | WO 96/10411 | 4/1996 |
| WO | WO 97/06685 | 2/1997 |
| WO | WO 97/06821 | 2/1997 |
| WO | WO 97/06828 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/46743 | 10/1998 |
| WO | WO 99/29834 | 6/1999 |
| WO | WO 99/50303 | 10/1999 |
| WO | WO 00/54801 | 9/2000 |
| WO | WO 01/91787 | 6/2001 |
| WO | WO 01/92474 | 12/2001 |
| WO | WO 02/15930 | 2/2002 |
| WO | WO 02/30434 | 4/2002 |
| WO | WO 02/32923 | 4/2002 |
| WO | WO 02/34205 | 5/2002 |
| WO | WO 03/090686 | 11/2003 |
| WO | WO 03/092624 | 11/2003 |
| WO | WO 2004/075636 | 9/2004 |

OTHER PUBLICATIONS

Binder et al., 2002 "Naturally formed or artificially reconstituted non-covalent alpha2-macroglobulin-peptide complexes elicit CD91-dependent cellular immunity." *Cancer Immun.* Dec. 18;2:16-24.

Bumol et al., 1988 "Characterization Of The Human Tumor And Normal Tissue Reactivity Of The KS1/4 Monoclonal Antibody." *Hybridoma* 7:407-415.

Carswell et al., 1970, "Immunogenic Properties Of Reticulum Cell Sarcomas Of SJL/J Mice." *Natl. Cancer Inst.* 44:1281-1288.

Cassel et al., 1983 "A Phase II Study On The Postsurgical Management Of Stage II Malignant Melanoma With A Newcastle Disease Virus Oncolysate." *Cancer*, 52:856-860.

Dash, et al., 2002 "Slow-Tight Binding Inhibition of Xylanase by an Aspartic Protease Inhibitor." *J. Biol. Chem.* 277:17978-17986.

Deutscher et al., 1992 "Guide to protein purification." *Meth. Enzymol.*, 182:779-780.

Dubois, et al., 1982 "Purification and Biochemical Properties of Tumor-Associated Transplantation Antigens From Methylcholanthrene-Induced Murine Sarcomas." *Proc. Natl. Acad. Sci USA*, 79:7669-7673.

Graham, et al. 1955,, "Antibodies Elicited by Cancer in Patients.", *Cancer* 8:409-416.

Griffen, Jr., et al. 1972, "Colon Carcinoma and Immunologic Phenomena." *Surgical Clinics of North America*, vol. 52:839-846.

Grobmann et al., 1997, "Active-Specific Immunotherapy Of Pancreatic Carcinoma: Usefulness Of Human Pancreatic Carcinomas In Preparing Autologous Tumor Vaccines." *Anticancer Res.* 17: 3117-3120.

Heiskala et al., 1988 "Characteristics Of Soluble Tumour-Derived Proteins That Inhibit Natural Killer Activity." *Scand. J. Immunol.* 28:19-27.

Henttu and Vihko, 1989 "cDNA Coding For The Entire Human Prostate Specific Antigen Shows High Homologies To The Human Tissue Kallikrein Genes." *Biochem. Biophys. Res. Comm.* 160:903-910.

Hughes et al., 1970, "A Study In Clinical Cancer Immunotherapy", *Cancer*, 26:269-278.

Israeli et al., 1993, "Molecular Cloning Of A Complementary DNA Encoding A Prostate-Specific Membrane Antigen." *Cancer Res.* 53:227-230.

Jocham et al.,2004, "Adjuvant Autologous Renal Tumour Cell Vaccine and Risk of Tumour Progression in Patients with Renal-Cell Carcinoma After Radical Nephrectomy: Phase III, Randomised Controlled Trial." *The Lancet*, vol. 363:594-599.

Kripke, 1974 "Antigenicity Of Murine Skin Tumors Induced By Ultraviolet Light." *J. Natl. Cancer Inst.* 53:1333-1336.

Livingston et al. 1985,, "Serological Response of Melanoma Patients to Vaccines Prepared from VSV Lysates of Autologous and Allogeneic Cultured Melanoma Cells." *Cancer*, 55:713-720.

Murray et al., 1977 "Viral Oncolysate in the Management of Malignant Melanoma II, Clinical Studies." *Cancer* 40:680-686.

Nair et al., 1977 "Antigen-Presenting Cells Pulsed With Unfractionated Tumor-Derived Peptides Are Potent Tumor Vaccines." *Eur. J. Immunol.* 27:589-597.

Natali et al., 1987 "Immunohistochemical Detection Of Antigen In Human Primary And Metastatic Melanomas By The Monoclonal Antibody 140.240 And Its Possible Prognostic Significance." *Cancer*, 59:55-63.

Oettgen and Old, 1991 "The History Of Cancer Immunotherapy." In: *Introduction To The Biologic Therapy Of Cancer*, Devitta et al., Eds., Lippincott, Philadelphia, PA, pp. 87-119 (Chapter 6).

Old et al., 1962 "Part II. Antigens Of Tumor Cells. Antigenic Properties Of Chemically-Induced Tumors." *Ann. N.Y. Acad. Sci.* 101:80-106.

Pattillo, 1974 "Combination Chemotherapy-Immunotherapy Indirect Chemotherapy Sensitivity Testing and Specific and Non-Specific Immunostimulation." In: *Neoplasm Immunity: Theory and Application: Proceedings of a Chicago Sumposium*, Crispen, Ed. ITR, Chicago, IL, pp. 189-204.

Paul, Ed., 1993 *Fundamental Immunology*, 3rd Edition, Raven Press, NY, p. 1158 and References 189-220 Cited On pp. 1173-1174.

Perez and Walker, 1989, "Isolation And Characterization Of A CcDNA Encoding The KS1/4 Epithelial Carcinoma Market", *J. Immunol.* 142:3662-3667.

Prehn and Main, 1957 "Immunity To Methylcholanthrene-Induced Sarcomas." *J. Natl. Cancer Inst.* 18:769-778.

Repmann et al. 1997 "Adjuvant Therapy Of Renal Cell Carcinoma With Active-Specific-Immunotherapy (ASI) Using Autologous Tumor Vaccine." *Anticancer Res.* 17:2879-2882.

Schreiber, 1989 "Tumor Immunology." In: *Fundamental Immunology*, 2nd Edition, Paul, ed. , pp. 923-955.

Tailor et al., 1990, "Nucleotide Sequence Of Human Prostatic Acid Phosphatase Determined From A Full-Length cDNA Clone." *Nucl. Acids Res.* 18:4928 (1990).

Vaage, 1968 "Nonvirus-Associated Antigens In Virus-Induced Mouse Mammary Tumors." *Cancer Res.* 28:2477-2483.

Vijayasaradhi et al., 1990 "The Melanoma Antigen gp75 Is The Human Homologue Of The Mouse *b* (Brown) Locus Gene Product." *J. Exp. Med.* 171:1375-1380.

Xiao et al., 1995, "Characterization of hormonogenic sites in an N-terminal, cyanogen bromide fragment of human thyroglobulin." *Arch Biochem Biophys.* 20;320(1):96-105.

Office Action dated Aug. 7, 2006 for U.S. Appl. No. 10/784,012.

Office Action dated Feb. 22, 2007 for U.S. Appl. No. 10/784,012.

Andus et al., Synthesis of alpha 2-macroglobulin in rat hepatocytes and in a cell-free system. FEBS Lett. Jan. 10, 1983;151(1):10-14.

Lodish et al., *Molecular Cell Biology*, ch. 17.3 "Overview of the Secretory Pathway". pp. 691-696, W.H. Freeman and Company 2000.

Office Action dated Nov. 2, 2007 for U.S. Appl. No. 10/784,012.

Basu et al., CD91 is a common receptor for heat shock proteins gp96, hsp90, hsp70, and calreticulin. Immunity. Mar. 2001; 14(3):303-13.

Borth W. Alpha 2-macroglobulin, a multifunctional binding protein with targeting characteristics, FASEB J. Dec. 1992; 6(15):3345-53.

Bukau et al., The Hsp70 and Hsp60 chaperone machines. Cell. Feb. 6, 1998; 92(3):351-66.
Sottrup-Jensen et al., Primary structure of human alpha 2-macroglobulin. J Biol Chem. Jul. 10, 1984; 259(13):8318-27.
U.S. Appl. No. 09/693,643, filed Oct. 20, 2000, Srivastava.
Aldovini et al., 1992, "The New Vaccines", *Technology Review* pp. 24-31.
Amato et al., 1999, "Active Specific Immunotherapy in Patients with Renal Cell Carcinoma (RCC) Using Autologous Tumor Derived Heat Shock Protein-Peptide Complex-96 (HSPP-96) Vaccine" *American Society Clinical Oncology Meeting*, abstract 1278.
Andersen, P. 1994, "Effective vaccination of mice against *Mycobacterium tuberculosis* infection with a soluble mixture of secreted mycobacterial proteins," Infect. Immun. 62(6):2536-44.
Anthony et al., 1999, "Priming of CD8+ CTL effector cells in mice by immunization with a stress protein-influenza virus nucleoprotein fusion molecule," Vaccine 17(4):373-83.
Arnold et al., 1995, "Cross-priming of minor histocompatibility antigen-specific cytotoxic T cells upon immunization with the heat shock protein gp96", J Exp Med. Sep 1;182(3):885-9.
Arnold-Schild et al., 1999, "Cutting edge: receptor-mediated endocytosis of heat shock proteins by professional antigen-presenting cells", J. Immunol. 162: 3757-3760.
Asea et al., 2000, "HSP70 stimulates cytokine production through a CD14-dependent pathway, demonstrating its dual role as a chaperone and cytokine," Nature Medicine 6:435-442.
Banchereau et al., 1998, "Dendritic cells and the control of immunity," Nature 392:245-252.
Barrios et al,, 1992, "Mycobacterial heat-shock proteins as carrier molecules, II; The use of the 70-kDa mycobacterial heat-shock protein as carrier for conjugated vaccines can circumvent the need for adjuvants and *Bacillus calmette* Guerin priming," Eur. J. Immunol. 22(6):1365-72.
Barrios et al., 1994, "Heat shock proteins as carrier molecules: in vivo helper effect mediated by *Escherichia coli* GroEL and Dna K proteins requires cross-linking with antigen," Clin. Exp. Immunol. 98(2):229-233.
Barrios et al., 1994, "Specificity of antibodies induced after immunization of mice with the mycobacterial heat shock protein of 65 kD." Clin. Exp Immunol. 98(2):224-8.
Basombrio (1970) "Search for common antigenicities among twenty-five sarcomas induced by methylcholanthrene", *The Institute for Cancer Research* 30:2458-2462.
Basu and Srivastava, 1999, "Calreticulin, a peptide-binding chaperone of the endoplasmic reticulum, elicits tumor- and peptide-specific immunity" *J. Exp. Med.* 189:797-802.
Basu et al., 2000, "Necrotic but not apoptotic cell death releases heat shock proteins, which deliver a partial maturation signal to dendritic cells and activate the NF-kappa B pathway," Int. Immunol. 12(11):1539-46.
Bevan, 1995, "Antigen presentation to cytotoxic T lymphocytes in vivo", J.Exp. Med. 192: 639-41.
Bhattacharjee et al., 1999, "Incorporation of non-proteolytic proteins by murine α-2 macroglobulin", Biochirnica et Biophysica Acta 1432:49-56.
Binder et al., 1998, Cell Stress & Chaperones 3 (Supp. 1): 2.
Binder et al., 2001, "Adjuvanticity of $\alpha_3$-Macroglobulin, an Independent Ligand for the Heat Shock Protein Receptor CD91," J. Immunol. 166(8):4968-4972.
Birkenmeier G., 2001, "Targetting the Proteinase Inhibitor and Immune Modulatory Function of Human α2-Macroglobulin." Mod. Asp. Immunobiol. 2(1):32-36.
Blachere and Srivastava (1993) "Immunization with GP96 heat shock proteins isolated from tumors or influenza virus infected cells elicits MHC-restricted, antigen-specific cytotoxic T lymphocytes against the corresponding cells", *J. Cellular Biochem. Keystone Symposia*, 17D: pp. 124, Abstract NZ 502.
Blachere et al., 1993, "Heat Shock Protein Vaccines Against Cancer," *Journal of Immunotherapy* 14:352-356.
Blachere et al., 1997, "Heat shock protein-peptide complexes reconstituted in vitro, elicit peptide-specific cytotoxic T lymphocyte response and tumor immunity," J. Exp. Med. 186(8):1315-22.

Blander et al., 1993, "Major cytoplasmic membrane protein of Legionella pnumophila, a genus common antigen and member of the hsp 60 family of heat shock proteins, induces protective immunity in a guinea pig model of Legionnaires' disease," J. Clin. Invest. 91(2):717-23.
Breloer et al., 1999, "in vivo and in vitro activation of T cells after administration of Ag-negative heat shock proteins," *J. Immunol.* 162:3141-3147.
Cassel et al., 1977, "Viral oncolysate in the management of malignant melanoma, I. Preparation of the oncolysate and measurement of immunologic responses," Cancer 40:672-679.
Castellino et al., 2000, "Receptor-mediated Uptake of Antigen/Heat Shock Protein Complexes Results in Major Histocompatibility Complex Class I Antigen Presentation via Two Distinct Processing Pathways", J. Exp. Med. 191:1957-64.
Chen et al., 1999, "Human 60-kDa heat-shock protein: a danger signal to the innate immune system," J. Immunol. 162:3212-3219.
Chu et al., 1994, "alpha 2-Macroglobulin, complement, and biologic defense: antigens, growth factors, microbial proteases, and receptor ligation". Lab Invest. 71(6):792-812.
Chu and Pizzo, 1993, "Receptor-Mediated Antigen Delivery into Macrophages," J. Immunol. 150(I):48-58.
Chu and Pizzo, 1994, "$\alpha_2$-Macroglobulin, Complement, and Biologic Defense: Antigens. Growth Factors, Microbial Proteases, and Receptor, Ligation," Lab. Invest. 71:792-812.
Chu et al., 1994, "Adjuvant-Free In Vivo Targeting Antigen Delivery by α-Macroglobulin Enhances Antibody Formation," J. Immunol. 152(4):1538-1545.
Chu et al., 1994, $\alpha_2$-Macroglobulin: A Sensor for Proteolysis, Ann. N.Y. Acad. Sci. 737:291-307.
Ciupitu et al., 1998, "Immunization with lymphocytic choriomeningitis virus peptide mixed with heat shock protein 70 results in protective antiviral immunity and specific cytotoxic T lymphocytes", J Exp Med. 187(5):685-91.
Clarke et al. 1988, "Purification of Complexes of Nuclear Oncogene p53 with Rat and *Escherichia coli* Heat Shock Proteins: In Vitro Dissociation of hsc70 and dnaK from Murine p53 by ATP" Mol. and Cell. Biol. vol. 8 (3)1206-1215.
Coutiho et al., 1998, "Alpha-2-macroglobulin receptor is differently expressed in peritoneal macrophages from C3H and C57/B16 mice and up-regulated during *Trypanosoma cruzi* infection", Tissue and Cell 30: 407-15.
Craig, 1993, "Chaperones: Helpers Along the Pathways to Protein Folding," Science 260:1902-4.
Davidoff et al., 1992, Immune response to p53 is dependent upon p53/HSP70 complexes in breast cancers.
Day et al., 1997, "Direct delivery of exogenous MHC class I molecule-binding oligopeptides to the endoplasmic reticulum of viable cells", Proc Natl Acad. Sci. USA 94: 8064-8069.
Del Giudice et al., 1994, "Hsp70: a carrier molecule with built-in adjuvanicity", Experientia 30;50(11-12):1061-6.
Dennis et al., 1989, "Alpha 2-macroglobulin is a binding protein for basic fibroblast growth factor", J Biol Chem. 264(13):7210-6.
DuBois et al., 1980, "Immunogenic properties of soluble cytosol fractions on Meth A sarcoma cell," Cancer Res. 40:4204-4208.
Estin et al., 1989, "Transfected mouse melanoma lines that express various levels of human melanoma-associated antigen p97," J. Natl. Cancer Inst. 81:445-448.
Falk et al., 1990, "Cellular Peptide Composition Governed by Major Histocompatibility Complex Class I Molecules", *Nature* 348:248-251.
Falk et al., 1991, "Identification of Naturally Processed Viral Nonapeptides Allows Their Quantification in Infected Cells and Suggests an Allele-specific T Cell Epitope Forecast". J Exp. Med 174:425-434.
Falk et al., 1991, "Allele-specific Motifs Revealed by Sequencing of Self-peptides Eluted from MHC Molecules", *Nature* 351:290-296.
Falk et al., 1992, "Specificity of antigen processing for MHC class I restricted presentation is conserved between mouse and man", Eur. J. Immunol. 22:1323-1326.
Fedweg and Srivastava "Evidence for biochemical heterogeneity of gp96 heat shock protein/tumor rejecion antigen", Mount Sinai School of Medicine NZ 206, p. 108, Mar. 1993.

Feng et al., 2002, "Exogenous heat shock proteins provide adjuvant effects on enhancing the immunogenicity of apoptotic tumor cells and inducing antitumor immunity," AACR 93rd Annual Meeting, vol. 43, Apr. 6-10, Abstract #2214.

Ferrero et al., 1995, The GroES homolog of *Helicobacter pylori* confers protective immunity against mucosal infection in mice. Proc Natl Acad Sci USA 92(14):6499-503.

Flynn et al., 1989, "Peptide binding and release by proteins implicated as catalysts of protein assembly", *Science* 245:385-390.

Flynn et al., 1991, "Peptide-binding Specificity of the Molecular Chaperone BiP", *Nature* 353:726-730.

Forrester et al., 1983, "Effect of modified alpha 2macroglobulin on leucocyte locomotion and chemotaxis", Immunology 50(2)251-9.

Gallucci et al., 1999, "Natural adjuvants: endogenous activators of dendritic cells," Nat. Med. 5:1249-55.

Gelber et al., 1992, "Vaccination of mice with a soluble protein fraction of *Mycobacterium leprae* provides consistent and long-term protection against M. leprae infection," Infect Immun. 60(5):1840-4.

Gelber et al., 1994, "Vaccination with pure *Mycobacterium leprae* proteins inhibits M. leprae multiplication in mouse footpads," Infect Immun. 62(10):4250-5.

Gething et al., 1992, "Protein folding in the cell," Nature 355:33-45.

Gomez et al., 1991, "Protective efficacy of a 62-kilodalton antigen, HIS-62, from the cell wall and cell membrane of *Histoplasma capsulatum* yeast cells." Infect Immun. 59(12):4459-64.

Gomez et al., 1992, "An 80-kilodalton antigen from *Histoplasma capsulatum* that has homology to heat shock protein 70 induces cell-mediated immune responses and protection in mice," Infect Immun. 60(7):2565-71.

Gomez et al., 1995, "Vaccination with recombinant heat shock protein 60 from *Histoplasma capsulatum* protects mice against pulmonary histoplasmosis." Infect Immun. 63 (7):2587-95.

Graner et al. 2000, "Immunoprotective activities of multiple chaperone proteins isolated from murine B-cell leukemia/lymphoma" Clin. Can. Res.6:909.

Graner et al., 2000, "Tumor-derived multiple chaperone enrichment by free-solution isoelectric focusing yields potent antitumor vaccines" Cancer Immunol. Immunother. 49:476.

Graner et al., 2003, "Tumor-derived chaperone-rich cell lysates are effective therapeutic vaccines against a variety of cancers," Cancer Immunol. Immunother. 52(4):226-234.

Gron and Pizzo, 1998, "Non proteolytic Incorporation of Protein Ligands into Human α2 rnacroglobulin: Implications for the binding mechanism of $\alpha_2$-macroglobulin", Biochem. 37:6009-6014.

Halevy et al. 1990, "Different Tumor-Derived p53 Mutants Exhibit Distinct Biological Activites", Science vol. 250 113-116.

Hall et al., 1981, "Proteolytic Cleavage Sites on $\alpha_2$-Macroglobulin Resulting in Proteinase Binding are Different for Trypsin and *Staphylococcus aureus* V-8 Proteinase," Biochem. Biophys. Res. Commun. 100(1):8-16.

Hinds et al., 1987, "Immunological Evidence for the Association of p53 with a Heat Shock Protein, hsc70, in p53-plus-ras-Transformed Cell Lines" Mol. and Cell. Biol. vol. 7 (8) 2863-2869.

Hinds et al., 1990, "Mutant p53 DNA Clones from Human Colon Carcinomas Cooperate with ras in Transforming Primary Rat Cells: A Comparison of the "Hot Spot" Mutant Phenotypes" Cell Growth and Differentiation vol. 1 571-580.

Hollinshead, 1988, "Immunotherapy," in: *Cancer: The Outlaw Cell*, LaFond, ed., American Chemical Society, Washington, DC pp. 237-250 (Chapter 14).

Holtet el al., 1994, "Recombinant $\alpha_2$M Receptor binding domain binds to the $\alpha_2$M receptor with high affinity", Ann NY Acad Sci. 737:480-2.

Holtet et al., 1994, "Receptor-binding domain of human $\alpha_2$-macroglobulin Expression, folding and biochemical characterization of a high-affinity recombinant derivative," FEBS Lett. 344:242-6.

Horwitz et al., 1995. Protective immunity against tuberculosis induced by vaccination with major extracellular proteins of *Mycobactenium tuberculosis*. Proc Natl Acad Sci U S A. 92(5):1530-4.

Huang et al., 1984, Specific covalent binding of platelet-derived growth factor to human plasma alpha 2-macroglobulin. Proc Natl Acad Sci U S A. 81(2):342-6.

Huang et al., 1996, "The immunodominant major histocompatibility complex class I-restricted antigen of a murine colon tumor derives from an endogenous retroviral gene product", Proc Natl Acad Sci U S A. 93(18):9730-5.

Hubbard et al., 1992, "Immunization of mice with mycobacterial culture filtrate proteins," Clin. Exp. Immunol. 87(1):94-8.

Humphrey et al., 1984, "Adjuvant immunotherapy for melanoma," J. Surg. Concol. 25:303-305.

Hunt et al., 1990, "Characterization and sequence of a mouse hsp70 gene and its expression in mouse cell lines", Gene 87(2):199-204.

Ishii et al., 1999, "Isolation of MHC class I-restricted tumor antigen peptide and its precursors associated with heat shock proteins hsp70, hsp90, and gp96", J Immunol. 162(3):1303-9.

Jakob et al., 1993, "Small Heat Shock Proteins Are Molecular Chaperones", *J. Biol. Chem.* 268:1517-1520.

Janetzki et al., 2000, "Immunization of cancer patients with autologous cancer-derived heat shock protein gp96 preparations: a pilot study" *Int. J. Of Cancer* 8:232-238.

Jardetzky et al., 1991, "Identification of Self Peptides Bound to Purified HLA-B27", *Nature* 353:326-329.

Jindal et al., 1989, Primary structure of a human mitochondrial protein homologous to the bacterial and plant chaperonins and to the 65-kilodalton mycobacterial antigen. Mol Cell Biol. 9(5):2279-83.

Katsanis et al., 2000, "Augmentation of Tumor Lysate Immunogencity by enrichment of Chaperone Proteins Using Free Solution Isoelectric Focusing (FS-IEF)" *Keystone Symposia on Cellular Immunity and Immunotherapy of Cancer*, abstract 431.

Kojima et al., 2002, "Combination therapy of tumor-derived gp96 and GM-CSF or IL-I2-gene transduced tumor cells in the control of LLC tumor," AACR 93rd Annual Meeting, vol. 43, Abstract #5516.

Kol et al., 2000, "Cutting edge: heat shock protein (HSP)60 activates the innate immune response: CD14 is an essential receptor for HSP60 activation of monocuclear cells", J Immunol. 164(1):13-17.

Kristensen et al., 1990, "Evidence that the newly cloned low-density-lipoprotein receptor related protein (LRP) is the alpha 2-macroglobulin receptor", FEBS Lett. 276(1-2):151-5.

Lakey et al., 1987, "Identification of a peptide binding protein that plays a role in antigen presentation", *Proc. Natl. Acad. Sci. USA* 84:1659-1663.

Lanzavecchia, 1993, "Identifying Strategies for Immune Intervention", *Science* 260:937-944.

Lēvy, 1991, "ATP is Required for In Vitro Assembly of MHC Class I Antigens but Not for Transfer of Peptides across the ER Membrane", *Cell* 67:265-274.

Li and Srivastava, 1993, "Tumor rejection antigen gp96/grp94 is an ATPase: Implications for protein folding and antigen presentation", *EMBO J*, 12(8):3143-3151.

Lindquist et al., 1988, "The Heat-Shock Proteins," Ann. Rev. Genetics 22:631-77.

Luescher et al., 1991, "Specific Binding of Antigenic Peptides to Cell-associated MHC Class I Molecules", *Nature* 351:72-77.

Lukacs et al., 1993, "Tumor cells transfected with a bacterial heat-shock gene lose tumorigenicity and induce protection against tumors", *J. Exp. Med*. 178:343-348.

Lussow et al., 1991, "Mycobacterial heat-shock proteins as carrier molecules", Eur J Immunol. 21(10):2297-302.

Madden et al., 1991, "The Structure of HLA-B27 Reveals Nonamer Self-peptides Bound in an Extended Conformation", *Nature* 353:321-325.

Maki (1991) "The Human Homologue of the Mouse Tumor Rejection Antigen GP96", Ph.D. thesis, Cornell University.

Maki et al., 1990, "Human homologue of murine tumor rejection antigen gp96: 5'-regulatory and coding regions and relationship to stress-induced proteins", Proc Natl Acad Sci U S A. 87(15):5658-63.

Martin et al., 1986, "Role of Murine Tumor Models in Cancer Treatment Research", Cancer Research 46:2189-2192.

Matsutake et al., 2001, "The immunoprotective MHC II epitope of a chemically induced tumor harbors a unique mutation in a ribosomal protein," PNAS 98(7):3992-3997.

Melcher et al., 1998, "Tumor immunogenicity is determined by the mechanism of cell death via induction of heat shock protein expression", Nat. Med. 5:581-7.

Melief et al., 1992, "Lessons from T Cell Responses to Virus Induced Tumours for Cancer Eradication in General", *Career Surveys* 13:81-99.

Melnick, 1985, "Virus Vaccines: An Overview", Proceedings of the First Annual Southwest Foundation for Biomedical Research International Symposium, Houston, Texas, Nov. 8-10, 1984, *American Society for Microbiology* pp. 1-13.

Ménoret and Chandawarkar, 1998, "Heat-shock protein-based anti-cancer immunotherapy: an idea whose time has come" *Semin. in Oncology* 25:654.

Menoret et al., 1995, "Co-segregation of tumor immunogenicity with expression of inducible but not constitutive hsp70 in rat colon carcinomas," *J. Immunol.* 155:740-7.

Menoret et al., 1999, "Association of peptides with heat shock protein gp96 occurs in vivo and not after cell lysis", Biochem Biophys Res Commun. 262(3):813-8.

Misra et al., 1993, "Receptor-recognized alpha 2-macroglobulin-methylamine elevates intracellular calcium, inositol phosphates and cyclic AMP in murine peritoneal macrophages", Biochem J. 290 (Pt 3):885-91.

Mitsuda et al., 1993, "A receptor-mediated antigen delivery and incorporation system. Administration of alpha 2-macroglobulin-cyrochrome c conjugate induced high concentrations of antibodies against cytochrome c in mice." Biochem Biophys Res Commun. 191(3):1326-31.

Mizzen et al., 1998, "Immune responses to stress proteins: applications to infectious disease and cancer," Biotherapy 10:173-185.

Moestrup et al., 1992, "Distribution of the alpha 2-macroglobulin receptor/low density lipoprotein receptor-related protein in human tissues". Cell Tissue Res. 269(3):375-82.

Moestrup et al., 1993, "$\alpha$-$_2$macroglobulin-proteinase complexes, plasminogen activator inhibitor type-I-plasminogen activator complexes, and receptor-associated protein bind to a region of the $\alpha$-$_2$-macroglobulin receptor containing a cluster of eight complement type repeats", J. of Biolog. Chem. 268: 13691-13696.

Mulé et al., 1984, "Adoptive Immunotherapy of Established Pulmonary Metastases with LAK Cells and Recombinant Interleukin-2", Science 225:1487-1489.

Munro et al., 1986, "An Hsp70-like protein in the ER: identity with the 78 kd glucose-regulated protein and immunoglobulin heavy chain binding protein", Cell 46(2)291-300.

Nair et al., 1999, "Calreticulin displays in vivo peptide-binding activity and can elicit CTL responses against bound peptides" *J. Immunol.* 162:6426.

Nicchitta et al., 1998, "Biochemical, cell biological and immunological issues surrounding the endoplasmic reticulum chaperone GRP94/gp96", Curr Opin Immunol. 10(1):103-9.

Nieland et al., 1996, "Isolation of an immunodominant viral peptide that is endogenously bound to the stess protein GP96/GRP94", Proc. Natl. Acad. Sci. USA 93:6135/6139.

Nielsen et al., 1996, "Identification of Residues in $\alpha_2$-Macroglobulins Important for Binding to the $\alpha_2$-Macroglobulin Receptor/Low Density Lipoprotein Receptor-related Protein," J. Biol. Chem. 271:12909-12912.

Noguchi et al., 1994, "A Mouse p53 Product Recognized by CD4* and CD8* T Cells," PNAS 91:3171-3175.

Norbury et al., 1997, "Constitutive inacropinocytosis allows TAP-dependent major histocompatibility complex class I presentation of exogenous soluble antigen by bone marrow-derived dendritic cells", Eur J Immunol. 27(1):280-8.

Norrby, 1985, "Summary," in: *Vaccines 85*, Lerner et al., eds., Cold Spring Harbor Laboratory, Cold Spring Harbor, NY pp. 387-394.

Nykjaer et al., 1992, "Purified alpha 2-macroglobulin receptor/LDL receptor-related protein binds urokinase.plasminogen activator inhibitor type-1 complex. Evidence that the alpha 2-macroglobulin receptor mediates cellular degradation of urokinase receptor-bound complexes", J Biol Chem. 267(21):14543-6.

O'Connor-McCourt et al., 1987, "Latent transforming growth factor-beta in serum. A specific complex with alpha 2-macroglobulin", J Biol Chem. 262(29): 14090-9.

Ohashi et al., 2000, Cutting edge: heat shock protein 60 is a putative endogenous ligand of the toll-like receptor-4 complex. J. Immunol. 164:558-561.

Orit Pinhasi-Kimhi et al. 1986, "Specific interaction between the p53 cellular tumour antigen and major heat shock protiens", Nature vol. 320 (13) 182-184.

Orth et. al., 1992, "Complexes of tissue-type plasminogen activator and its serpin inhibitor plasminogen-activator inhibitor type 1 are internalized by means of the low density lipoprotein receptor-related protein/alpha 2-macroglobulin receptor", Proc Natl Acad Sci U S A. 89(16):7422-6.

Osada et al., 1987, "Murine T cell proliferation can be specifically augmented by macrophages fed with specific antigen: $\alpha_2$-Macroglobulin conjugate," Biochem. Biophys. Res. Commun. 146:26-31.

Osada et al., 1988, "Antibodies against viral proteins can be produced effectively in response to the increased uptake of alpha 2-macroglobulin:viral protein conjugate by macrophages", Biochem Biophys Res Commun. 150(2):883-9.

Otto A. et al., 1998, "Prostate-specific antigen forms complexes with human alpha 2-macroglobulin and binds to the alpha 2-macroglobulin receptor/LDL receptor-related protein." J. Urol, 159(1):297-303.

Pal P.G., et al., 1992, "Immunization with extracellular proteins of *Mycobacterium tuberculosis* induces cell-mediated immune responses and substantial protective immunity in a guinea pig model of pulmonary tuberculosis," Infect Immun. 60(11):4781-92.

Palladino et al., 1987 "Expression of shared tumor-specific antigen by two chemically induced BALB/c sarcomas", *Cancer Research* 47:5074-5079.

Pardoll, 2000. "Therapeutic vaccination for cancer", Clin. Immunol. 95(1 Pt 2): S44-62.

Peng et al., 1997, "Purification of immunogenic heat shock protein 70-peptide complexes by ADP-affinity chromatography" *J. Immunol. Meth.* 204:13.

Pinilla-Ibarz et al., 2000, "Vaccination of patients with chronic myelogenous leukemia with bcr-abl oncogene breakpoint fusion peptides generates specific immune responses," Blood 95(5): 1781-1787.

Qiu et al., 1999, "$\alpha$2 macroglobulin enhances the clearance of endogenous soluble $\beta$-amyloid peptide via low density lipoprotein receptor-related protein in cortical neurons", J. Neurochem. 73(4):1393-1398.

Rogers et al., 1981, "Some immunogenic acid biochemical properties of tumor-associated transplantation antigens (TATA) obtained in soluble form or solubilized from two methylcholanthrene-induced sarcomas, Meth A and CI-4, " Int. J. Cancer 27:789-796.

Rothman, 1989, "Polypeptide Chain Binding Proteins: Catalysts of Protein Folding and Related Processes in Cells", *Cell* 59:591-601.

Rötzschke et al., 1990, "Isolation and Analysis of Naturally Processed Viral Peptides as Recognized by Cytotoxic T cells", *Nature* 348:248-251.

Rotzschke, 1990, "Characterization of Naturally Occurring Minor Histocompatibility Peptides including H-4 and H-Y" Science 249: 283-287.

Salk et al., 1993, "A Strategy for Prophylactic Vaccination Against HIV", *Science* 260:1270-1272.

Sallusto et al., 1994, "Efficient presentation of soluble antigen by cultured human dendritic cells is maintained by granulocyte/macrophage colony-stimulating factor plus interleukin 4 and downregulated by tumor necrosis factor alpha," J. Exp. Med. 179(4):1109-1118.

Sano et al., 1987, "The augmentation of tumor-specific immunity using haptenic muramyl dipeptide (MDP) derivatives. II. Establishment of tumor-specific immunotherapy models utilizing MDP hapten-reactive helper T cell activity," Cancer Immunol. Immunother. 25(3):180-184.

Sauter et al., 2000, "Consequences of cell death: exposure to necrotic tumor cells, but not primary tissue cells or apoptotic cells, induces the maturation of immunostimulatory dendritic cells", J. Exp. Med. 191:423-434.

Schumacher et al., 1991, "Peptide Selection by MHC Class I Molecules", *Nature* 350:703-706.

Silva et al., 1994, "A single mycobacterial protein (hsp 65) expressed by a transgenic antigen-presenting cell vaccinates mice against tuberculosis", Immunology 82(2):244-8.

Singh-Jasjua et al., 2000, "Cross Presentation of Glycoprotein 96-associated antigens on major histocompatibility complex class I molecules requires receptor-mediated endocytosis", J. Exp. Med. 191:1965-74.

Soeiro et al., 2000, "Trypanosoma cruzi: Acute Infection Affects Expression of α-2-macroglobulin and A2MR/LRP Receptor Differently in C3H and C57BL/6 Mice", Exper. Parasitology 96:97-107.

Sorger and Pelham, 1987, "The glucose-regulated protein grp94 is related to heat shock protein hsp90", J. Mol. Biol. 194(2):341-4.

Sparks et al., 1976, "Immunology and adjuvant chemoimmunotherapy of breast cancer," Arch. Surg, 111:1057-1062.

Srivastava and Heike, 1986, "Tumor-specific immunogenicity of stress-induced proteins: Convergence of two evolutionary pathways of antigen presentation?", Seminars in Immunology 3:57-64.

Srivastava and Old (1989) "Gp96 Molecules: Recognition Elements in Tumor Immunity", Human Tumor Antigens and Specific Tumor Therapy, pp. 63-71.

Srivastava and Udono, 1994, "Heat shock protein-peptide complexes in cancer immunotherapy" *Curr. Opin. Immunol.* 6:728.

Srivastava et al. (1990) Immunization with Soluble Gp96 Antigens Elicits Tumor-Specific Cellular Immunity:, Cellular Immunity and the Immunotherapy of Cancer, pp. 307-314.

Srivastava et al., 1984, "The Serologically Unique Cell Surface Antigen of Zajdela Ascitic Hepatoma is also its Tumor-Associated Transplantation Antigen", *Int. J. Cancer* 33:417-422.

Srivastava et al., 1986, "Tumor rejection antigens of chemically induced sarcomas of inbred mice," Proc. Natl. Acad. Sci. USA 83(10):3407-3411.

Srivastava et al., 1987, "5'-structural analysis of genes encoding polymorphic antigens of chemically induced tumors." Proc. Natl. Acad. Sci USA 84(11):3807-3811.

Srivastava et al., 1988, "Chromosomal assignment of the gene encoding the mouse tumor rejection antigen gp96," Immunogenetics 28:205-207.

Srivastava et al., 1988, "Individually distinct transplantation antigens of chemically induced mouse tumors," Immunol. Today 9:78-83.

Srivastava et al., 1989, "Identification of a Human Homologue of the Murine Tumor Rejection Antigen GP96," *Cancer Res.* 49:1341-1343.

Srivastava et al., 1991, "Protein Tumor Antigens", *Curr. Opin. Immunol.* 3:654-658.

Srivastava et al., 1991, "Stress-Induced Proteins in Immune Response to Cancer," Curr. Top. Microbiol. Immunol. 167:109-123.

Srivastava et al., 1993, "Evidence for peptide-chaperoning by the endoplasmic reticular heat shock protein GP96: Implications for vaccination against cancer and infectious diseases", *J. Cell Biochem Suppl* 17D:94 (Abstract NZ014).

Srivastava et al., 1994, "Heat shock proteins transfer peptides during antigen processing and CTL priming", Immunogenetics. 39(2):93-8. Review.

Srivastava et al., 1998, "Heat shock proteins come of age: primitive functions acquire new roles in an adaptive world", Immunity 8(6):657-65.

Srivastava PK, 1994, "Heat shock proteins in immune response to cancer: the Fourth Paradigm", Experientia. (11-12):1054-60.

Srivastava, 1993, "Peptide-Binding Heat Shock Proteins in the Endoplasmic Reticulum: Role in Immune Response to Cancer and in Antigen Presentation," Adv. Cancer Res. 62:153-177.

Srivastava, P.K. et al., 1998, "Chromosomal assignment of the gene encoding the mouse tumor rejection antigen gp96," Immunogenetics 28:205-207.

Stack et al., 1982, "Autologous x-irradiated tumour cells and percutaneous BCG in operable lung cancer," Thorax 37(8):588-593.

Stevenson, 1999, "DNA vaccines against cancer: from genes to therapy." Ann. Oncol. 10:1413-8 Review.

Strickland et al., 1990, "Sequence identity between the alpha 2-macroglobulin receptor and low density lipoprotein receptor-related protein suggests that this molecule is a multifunctional receptor", J Biol Chem. 265(29):17401-4.

Subbarao et al., 1992. "A General Overview of Viral Vaccine Development," *Genetically Engineered Vaccines* 327:51-57.

Suto et al., 1995, "A Mechanism for the Specific Immunogenicity of Heat Shock Protein-Chaperoned Peptides," Science 269:1585-8.

Suzue et al., 1997, "Heat shock fusion proteins as vehicles for antigen delivery into the major histocompatibility complex class I presentation pathway," Proc. Natl. Acad. Sci. USA 94(24):13146-51.

Suzue K., Young R.A., 1996, "Heat shock proteins as immunological carriers and vaccines. in: Stress-Inducible Cellular Responses" (U. Feige. R. I. Morimoto, I. Yahara, B. S. Potla, eds.), Birkhauser/ Springer, 77: 451-465.

Suzue K., Young R.A., 1996, "Adjuvant-free hsp70 fusion protein system elicits humoral and cellular immune responses to HIV-1" p. 24, J Immunol. 156(2):873-9.

Tamura et al., 1997, "Immunotherapy of tumors with autologous tumor-derived heat shock protein preparations", Science 278(5335):117-20.

Thomas et al., 1982, "Molecular and Cellular Effects of Heat Shock and Related Treatments of Mammalian Tissue-Culture Cells", *Cold Springs Harbor Symp Quant Biol* 46:985-996.

Tedryk et al., 1999, "Heat shock protein 70 induced during tumor cell killing induces Th1 cytokines and targets immature dendritic cell precursors to enhance antigen uptake," J. Immunol. 163:1398-1408.

Udono and Srivastava, 1993, "Heat Shock Protein 70-associated Peptides Elicit Specific Cancer Immunity," J. Exp. Med. 178(4):1391-1396.

Udono et al., 1994, "Cellular requirements for tumor-specific immunity elicited by heat shock proteins: tumor rejection antigen gp96 primes CD8+ T cells in vivo", Proc. Natl. Acad. Sci. USA 91(8):3077-81.

Udono et al., 1994, "Comparison of Tumor-Specific Immunogenicities of Stress-Induced Proteins gp96,hsp90, and hsp70," J. Immunol., 152(11):5398-5403.

Udono, 1993, "Heat shock proteins HSP70, HSP90 and GP96 elicit tumor specific immunity to the tumors from which they are isolated", *J. Cell. Biochem. Suppl.* 17D:113 (Abstract NZ225).

Ullrich et al., 1986, "A mouse tumor-specific transplantation antigen is a heat shock-related protein," Proc. Natl. Acad. Sci. USA 83(10):3121-3125.

Vanbuskirk et al., 1989, "Peptide binding protein having a role in antigen presentation is a member of the hsp70 heat shock family", *J. Exp. Med.* 170:1799-1809.

Wallny et al., 1992, "Gene transfer experiments imply instructive role of major histocompatibility complex class I molecules in cellular peptide processing", Eur. J. Immunol 22:655-659.

Wang et al., 2001, "Characterization of heat shock protein 110 and glucose-regulated protein 170 as cancer vaccines and the effect of fever-range hyperthermia on vaccine activity," J. Immunol. 166(1):490-497.

Wassenberg et al., 1999, "Receptor mediated and fluid phase pathways for internalization of the ER Hsp90 chaperone GRP94 in murine macrophages," J. Cell Science 112:2167-2175.

Welch et al., 1982, "Purification of the Major Mammalian Heat Shock Proteins", *J. Biol. Chem.* 257:14949-14959.

Welch et al., 1985, "Rapid Purification of Mammalian 70,000-Dalton Stress Proteins: Affinity of the Proteins for Nucleotides", *Mol. Cell. Biol.* 5:1229-1237.

Welch et al., 1995, "Morphological study of the mammalian stress response: characterization of changes in cytoplasmic organelles, cytoskeleton, and nucleoli, and appearance of intranuclear actin filaments in rat fibroblasts after heat-shock treatment," J. Cell. Biol. 101:1198-1211.

Welch, 1993, "How Cells Respond to Stress," Scientific American 268(5):56-64.

Wu et al., 1998, "Oxidized $α_2$-Macroglobulin ($α_2$M) Differentially Regulates Receptor Binding by Cytokines/Growth Factors: Implications for Tissue Injury and Repair Mechanisms in Inflammation", J.Immun. 4356-4365.

Yamazaki et al., 1989, "Nucleotide sequence of a full-length cDNA for 90 kDa heat-shock protein from human peripheral blood lymphocytes", Nucleic Acids Res. 17(17):7108.

Yang et al., 1999, "Murine dendritic cells transfected with human GP100 elicit both antigen-specific CD8+ and CD4+ T-cell responses and are more effective than DNA vaccines at generating anti-tumor immunity," Int. J. Cancer 83:532-540.

Yedavelli et al., 1999, "Preventive and therapeutic effect of tumor derived heat shock protein, gp96, in an experimental prostate cancer model" *Int. J. Mol. Med.* 3:243.

Young, 1990, "Stress proteins and immunology," Annu. Rev. Immunol. 8:401-420.

Yu et al., 1991, "Sequence Analysis of Peptides Bound to MHC Class II Molecules", *Nature* 353:622-627.

* cited by examiner

METHODS FOR PREPARING COMPOSITIONS COMPRISING HEAT SHOCK PROTEINS USEFUL FOR THE TREATMENT OF CANCER AND INFECTIOUS DISEASE

The present invention claims the benefits of United States provisional patent applications ser. No. 60/313,629, filed Aug. 20, 2001, and ser. No. 60/337,222, filed Dec. 6, 2001, which are incorporated by reference herein in their entireties.

This invention was made with government support under grant number CA/A184479 awarded by the National Institutes of Health. The Government has certain rights in the invention.

1. INTRODUCTION

The present invention relates to methods and compositions for the prevention and treatment of infectious diseases, and primary and metastatic neoplastic diseases. In the practice of the prevention and treatment of infectious diseases and cancer, compositions comprising cytosolic and membrane-derived proteins from antigenic cells and/or the digestion products thereof, are complexed to heat shock proteins and/or alpha-2-macroglobulin to augment the immune response to tumors and infectious agents.

2. BACKGROUND OF THE INVENTION

2.1. Heat Shock Proteins

Heat shock proteins (HSPs), also referred to as stress proteins, were first identified as proteins synthesized by cells in response to heat shock. HSPs have been classified into five families, based on molecular weight, HSP100, HSP90, HSP70, HSP60, and smHSP. Many members of these families were found subsequently to be induced in response to other stressful stimuli including nutrient deprivation, metabolic disruption, oxygen radicals, and infection with intracellular pathogens (see Welch, May 1993, Scientific American 56-64; Young, 1990, Annu. Rev. Immunol. 8:401-420; Craig, 1993, Science 260:1902-1903; Gething et al., 1992, Nature 355:33-45; and Lindquist et al., 1988, Annu. Rev. Genetics 22:631-677).

Studies on the cellular response to heat shock and other physiological stresses revealed that the HSPs are involved not only in cellular protection against these adverse conditions, but also in essential biochemical and immunological processes in unstressed cells. HSPs accomplish different kinds of chaperoning functions. For example, members of the HSP70 family, located in the cell cytoplasm, nucleus, mitochondria, or endoplasmic reticulum (Lindquist et a/, 1988, Ann. Rev. Genetics 22:631-677), are involved in the presentation of antigens to the cells of the immune system, and are also involved in the transfer, folding and assembly of proteins in normal cells. HSPs are capable of binding proteins or peptides, and releasing the bound proteins or peptides in the presence of adenosine triphosphate (ATP) or acidic conditions (Udono and Srivastava, 1993, J. Exp. Med. 178:1391-1396).

Srivastava et al. demonstrated immune response to methylcholanthrene-induced sarcomas of inbred mice (1988, Immunol. Today 9:78-83). In these studies, it was found that the molecules responsible for the individually distinct immunogenicity of these tumors were glycoproteins of 96 kDa (gp96) and intracellular proteins of 84 to 86 kDa (Srivastava et al., 1986, Proc. Natl. Acad. Sci. USA 83:3407-3411; Ullrich et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205-207; Srivastava et al., 1991, Curr. Top. Microbiol. Immunol. 167:109-123). Further, HSP70 was shown to elicit immunity to the tumor from which it was isolated but not to antigenically distinct tumors. However, HSP70 depleted of peptides was found to lose its immunogenic activity (Udono and Srivastava, 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153-177; Udono et al., 1994, J. Immunol., 152:5398-5403; Suto et al., 1995, Science 269:1585-1588).

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (U.S. Pat. No. 5,750,119 issued May 12, 1998, and U.S. Pat. No. 5,837,251 issued Nov. 17, 1998, respectively, each of which is incorporated by reference herein in its entirety). The isolation and purification of HSP-peptide complexes has been described, for example, from pathogen-infected cells, and used for the treatment and prevention of infection caused by the pathogen, such as viruses, and other intracellular pathogens, including bacteria, protozoa, fungi and parasites (see, for example, PCT Publication WO 95/24923, dated Sep. 21, 1995). Immunogenic stress protein-antigen complexes can also be prepared by in vitro complexing of stress protein and antigenic peptides, and the uses of such complexes for the treatment and prevention of cancer and infectious diseases has been described in PCT publication WO 97/10000, dated Mar. 20, 1997 (U.S. Pat. No. 6,030,618 issued Feb. 29, 2000). The use of stress protein-antigen complexes for sensitizing antigen presenting cells in vitro for use in adoptive immunotherapy is described in PCT publication WO 97/10002, dated Mar. 20, 1997 (see also U.S. Pat. No. 5,985,270 issued Nov. 16, 1999).

2.2. Alpha-2-Macroglobulin

The α-macroglobulins are members of a protein superfamily of structurally related proteins which also comprises complement components C3, C4 and C5. The human plasma protein alpha-2-macroglobulin (α2M) is a 720 kDa homotetrameric protein primarily known as proteinase inhibitor and plasma and inflammatory fluid proteinase scavenger molecule (for review see Chu and Pizzo, 1994, Lab. Invest. 71:792). α2M is synthesized as a precursor having 1474 amino acid residues. The first 23 amino acids function as a signal sequence that is cleaved to yield a mature protein with 1451 amino acid residues (Kan et al., 1985, Proc. Natl. Acad. Sci. U.S.A. 82:2282-2286).

α2M promiscuously binds to proteins and peptides with nucleophilic amino acid side chains in a covalent manner (Chu et al., 1994, Ann. N.Y. Acad. Sci. 737:291-307) and targets them to cells which express a α2M receptor (α2MR) (Chu and Pizzo, 1993, J. Immunol. 150:48). Binding of α2M to the α2M receptor is mediated by the carboxy-terminal portion of α2M (Holtet et al., 1994, FEBS Lett. 344:242-246) and key residues have been identified (Nielsen et al., 1996, J. Biol. Chem. 271:12909-12912).

Generally known for inhibiting protease activity, α2M binds to a variety of proteases through multiple binding sites (see, e.g., Hall et al., 1981, Biochem. Biophys. Res. Commun. 100(1):8-16). Protease interaction with α2M results in a complex structural rearrangement called transformation, which is the result of a cleavage within the "bait" region of α2M after the proteinase becomes "trapped" by thioesters. The conformational change exposes residues required for receptor binding, allowing the α2M-proteinase complex to bind to the α2MR. Methylamine can induce similar conformational changes and cleavage as that induced by proteinases. The uncleaved form of α2M, which is not recognized by the receptor, is often referred to as the "slow" form (s-α2M). The cleaved form is referred to as the "fast" form (f-α2M) (reviewed by Chu et al., 1994, Ann. N.Y. Acad. Sci. 737:291-307). Recently, it has also been shown that the α2MR can bind to HSPs, such as gp96, hsp90, hsp70, and calreticulin (Basu et al., 2001, Immunity 14(3):303-13).

Studies have shown that in addition to its proteinase-inhibitory functions, α2M, when complexed to antigens, can enhance the antigens' ability to be taken up by antigen presenting cells such as macrophages and presented to T cell hybridomas in vitro by up to two orders of magnitude (Chu and Pizzo, 1994, Lab. Invest. 71:792), and to induce T cell proliferation (Osada et al., 1987, Biochem. Biophys. Res. Commun. 146:26-31). Further evidence suggests that complexing antigen with α2M enhances antibody production by crude spleen cells in vitro (Osada et al., 1988, Biochem. Biophys. Res. Commun. 150:883), elicits an in vivo antibody responses in experimental rabbits (Chu et al., 1994, J. Immunol. 152:1538-1545) and mice (Mitsuda et al., 1993, Biochem. Biophys. Res. Commun. 101:1326-1331). α2M-antigenic peptide complexes have also been shown to induce a cytotoxic T cell response in vivo (Binder et al., 2001, J. Immunol. 166:4698-49720).

3. SUMMARY OF THE INVENTION

The present invention encompasses methods for preparing complexes of antigenic proteins and peptides and heat shock protein (HSP) or alpha-2-macroglobulin (α2M) that are useful for the prevention and treatment of cancer and infectious disease.

In one embodiment, the invention provides a method of preparing complexes of HSPs and a population antigenic proteins of antigenic cells or viral particles. This method involves complexing a population of antigenic proteins derived from antigenic cells or viral particles to one or more different heat shock proteins in vitro, wherein the population comprises at least 50% of the different proteins or at least 50 different proteins that are present in the antigenic cells or viral particles, or present in a cellular fraction of the antigenic cells. In another embodiment, the method comprises contacting the protein preparation in vitro with one or more different heat shock proteins under conditions such that proteins in the protein preparation are complexed to the heat shock proteins.

In yet another embodiment, the invention provides complexes comprising HSPs and a population of antigenic peptides of antigenic cells or viral particles, wherein the population of antigenic peptides is generated by a method comprising digesting a protein preparation of antigenic cells, a cellular fraction thereof, or viral particles with either a protease or a plurality of different proteases separately. The population of antigenic peptides can also be generated by a method comprising exposing a protein preparation of antigenic cells, a cellular fraction thereof, or viral particles to ATP, guanidium hydrochloride, and/or acidic conditions sufficient to elute antigenic peptides from protein complexes present in the protein preparation. The antigenic peptides generated by either or both methods are complexed to one or more different HSPs in vitro.

In yet another embodiment, the invention provides a method of preparing complexes of α2M and a population of antigenic proteins of antigenic cells. This method involves complexing a population of antigenic proteins derived from antigenic cells or viral particles to α2M in vitro, wherein the population comprises at least 50% of the different proteins or at least 100 different proteins that are present in the antigenic cells or viral particles, or present in a cellular fraction of the antigenic cells. In another embodiment, the method comprises contacting the protein preparation in vitro with α2M under conditions such that proteins in the protein preparation are complexed to α2M.

In yet another embodiment, the invention provides complexes comprising α2M and a population of antigenic peptides of antigenic cells or viral particles, wherein the population of antigenic peptides is generated by a method comprising digesting a protein preparation of antigenic cells, a cellular fraction thereof, or viral particles, with either a protease or a plurality of different proteases separately. The population of antigenic peptides can also be generated by a method comprising exposing a protein preparation of antigenic cells, a cellular fraction thereof, or viral particles, with ATP, guanidium hydrochloride, and/or acidic conditions. The antigenic peptides generated by either or both methods are complexed to α2M in vitro.

In various embodiments, the antigenic cells can be cancer cells, or cells infected with a pathogen or infectious agent, and preferably human cells. The antigenic cells can also be cells of a pathogen or infectious agent, or variants thereof. The protein preparation of the antigenic cells may comprise only cytosolic proteins, only membrane-derived proteins, or both cytosolic and membrane-derived proteins. The protein preparation may be a crude, unfractionated cell lysate. In a specific embodiment, the protein preparation can be made by lysing the antigenic cells, removing cell debris and non-proteinaceous materials, and optionally purifying the proteins, by methods known in the art. In certain embodiments, the protein preparation has not been subjected to any method of preparation that selectively removes or retains one or more particular protein from the other proteins in the antigenic cells.

In certain embodiments, the protein preparation of the antigenic cells, a cellular fraction thereof, or viral particles can be digested by a variety of proteases, such as but not limited to trypsin, Staphylococcal peptidase I (also known as protease V8), chymotrypsin, pepsin, cathepsin G, thermolysin, elastase, and papain, under conditions suitable for enzymatic reaction. The extent of the digestion can be monitored by taking a sample and analyzing it by known techniques for determining the length of peptides. It is preferable that the digesting step is carried out under conditions such that the resulting population of peptides which comprises antigenic peptides, have an average size of from about 7 amino acid residues to about 20 amino acid residues. It is also desirable to generate from a protein preparation different populations of peptides by digesting aliquots of the protein preparation with different proteases. The peptides resulting from the different digests may be combined before complexing to HSP or α2M. Before complexing the population of peptides which comprises antigenic peptides to HSP or α2M, it may be desirable to inactivate or separate the protease from the population of peptides, and optionally purify the population of peptides.

In certain embodiments, the protein preparation of the antigenic cells, a cellular fraction thereof, or viral particles are contacted with adenosine triphosphate (ATP), guanidium hydrochloride, and/or acidic conditions such that antigenic peptides can be eluted without the need to isolate HSP complexes initially. The antigenic peptides eluted by this method comprise peptides that are endogenously associated with HSPs and MHC class I and II molecules.

In various embodiments of the invention, depending on the method used to complex the population of antigenic peptides to HSP or α2M, the reaction can result in the antigenic peptides complexed to HSP or α2M by either a covalent bond or non-covalent bond. Heat shock proteins that are contemplated for complexing include but not limited to HSP 60, HSP70, HSP 90, gp96, calreticulin, grp78 (or BiP), protein disulfide isomerase (PDI), HSP110, and grp170. Human HSPs and human α2M are generally preferred. The complexes of HSP and antigenic peptides can be further purified before their use in or as a therapeutic or prophylactic composition. Such compositions may further comprises an adjuvant. Kits comprising HSP and/or α2M, antigenic cells, protein preparations, and/or proteases are also provided.

In another embodiment of the invention, a method is provided for inducing an immune response in a subject against a first antigenic cell or viral particle comprising administering to the individual a composition comprising an immunogenic amount of HSP and/or α2M complexed to a population of antigenic proteins/peptides that were prepared from a second antigenic cell or viral particle. The antigenic peptides can be obtained by digesting the protein preparation of the antigenic cells or viral particles with a protease or exposing the protein preparation with ATP, guanidium hydrochloride and/or acidic condition. The first and second antigenic cells or viral particles express at least one common antigenic determinant.

In yet another embodiment, a method is provided for treating or preventing a type of cancer or infectious disease, comprising administering to a subject in need of such treatment or prevention a composition comprising an amount, effective for said treatment or prevention, of HSP and/or α2M complexed to a population of antigenic peptides. The antigenic proteins/peptides are prepared from cancer cells or cells infected with a pathogen that are antigenically related to the cancer or infectious diseases. A pathogen or infectious agent, including viral particles can also be used to prepare the antigenic peptides. The antigenic peptides can be obtained by digesting the protein preparation of the antigenic cells, a cellular fraction thereof or viral particles with a protease or exposing the protein preparation with ATP, guanidium hydrochloride and/or acid, such as trifluoroacetic acid.

In yet another embodiment, a method is provided for treating or preventing a type of cancer or infectious disease, comprising administering to a subject in need of such treatment or prevention antigen presenting cells which have been sensitized with complexes of HSP and/or α2M and a population of antigenic proteins/peptides. In addition to the sensitized antigen presenting cells, complexes of HSP and/or α2M and a population of antigenic peptides can also be administered to the subject.

In various embodiments, the administering of the complexes to a subject can be repeated at the same site, and periodically, for example, at weekly intervals. The composition can be administered by many routes, such as intradermally or subcutaneously.

4. DETAILED DESCRIPTION OF THE INVENTION

The present invention provides methods for preparing a composition comprising heat shock protein (HSP) or alpha-2-macroglobulin (α2M) that are useful for the prevention and treatment of cancer and infectious disease. The method of the invention comprises preparing in vitro complexes of HSP or α2M, and the antigenic proteins and peptides of antigenic cells. In one embodiment, the method involves making a protein preparation of the antigenic cells which preparation comprises a population of antigenic proteins; and complexing in vitro the population of antigenic proteins to HSP or α2M. In another embodiment, the method further involves digesting the protein preparation of the antigenic cells with at least one protease to generate a population of antigenic peptides prior to complexing in vitro the population of antigenicpeptides to HSP or α2M. The invention exploits the full antigenic potential of antigenic cells.

The therapeutic and prophylactic methods of the invention are based on eliciting an immune response in a subject in whom the treatment or prevention of infectious diseases or cancer is desired. The immune response is directed specifically against antigenic determinants of cancerous cells, cells infected by an infectious agent that causes the infectious disease, or antigenic determinants of the infectious agent. By administering to the individual a composition comprising HSPs and/or α2M complexed to peptides of an antigenic cell, the composition which comprises complexes of HSPs and/or α2M with antigenic peptides will stimulate an immune response, such as a cytotoxic T cell response. The antigenic cells can be cancerous cells or infected cells, or cells which share antigenic determinants with or display similar antigenicity as the cancerous or infected cells. As a result of the immune response, various immune effector mechanisms of the individual will act on the cancerous or infected cells which lead to the treatment or prevention of such disease.

The individual or subject in whom treatment or prevention of an infectious diseases or cancer is desired is an animal, preferably a mammal, a non-human primate, and most preferably human. The term "animal" as used herein includes but is not limited to farm animals or companion animals, such as cats, dogs, cows, pigs, sheep, horses, chickens, etc.

The therapeutic regimens and pharmaceutical compositions of the invention may be used in conjunction with additional immune response enhancers or biological response modifiers including, but not limited to, the cytokines IFN-α, IFN-γ, IL-2, IL-4, IL-6, TNF, or other cytokine that affects immune cells.

The compositions and methods of the present invention are an improvement over other compositions and methods that use naturally-occurring HSP-antigenic peptide complexes to treat or prevent cancer or infectious disease. In such other methods, a specific HSP and its complexes with antigenic peptides are isolated from a cancer or infected cell, and administered to a patient to induce an immune response against the cancer or infected cells in vivo (see e.g., U.S. Pat. Nos. 5,750,119 and 5,961,979). Naturally-occurring complexes are isolated by methods dictated by the type of HSP which is desired. Thus, naturally-occurring complexes of a type of HSP and antigenic peptides comprise only those antigenic peptides that are co-localized in a compartment of the antigenic cells with that type of HSP. Certain types of HSPs are found uniquely in one cellular compartment and some antigenic peptides are found only in certain compartments of an antigenic cell. For example, HSP90 and HSP70 are found only in the cytosol. Thus, they will only be complexed to antigenic peptides located in the cytosol but not to antigenic peptides located somewhere else, such as the endoplasmic reticulum for example. That is, only a subset of the antigenic peptides of the antigenic cell can bind to each particular HSP.

Thus, to stimulate an immune response to a maximum number of antigenic determinants of a cancer or infected cell, every type of HSPs and their peptide complex would have to be isolated from the cancerous or infected cell by their respective methods of isolation, and then administered to a patient. This approach is laborious and may require large amounts of antigenic cells which is not available under certain circumstances. The methods of the present invention solve this problem by generating a peptide profile of virtually all the antigens of an antigenic cell in vitro, and then complexing the peptides to one or more different HSP and/or α2M which can then be used to stimulate an immune response in a patient. By using the methods of the invention, even antigenic peptides and HSPs that are not co-localized within the same compartment of an antigenic cell can form a complex. The methods of the invention afford the possibility to form complexes of a particular type of HSP with a majority of or even every antigenic peptides of an antigenic cell. Accordingly, a more effective immune response against antigenic cells can be induced by the compositions prepared by the methods of the invention. Moreover, this method does not require the prior isolation of HSP complexes and the associated peptides, thus, allowing the use of very small amount of starting material which is often limited in supply.

Moreover, the antigen profile of cancerous cells, infected cells, or pathogens may change over a period of time, e.g., even during a course of treatment. Many pathogens evade the host immune system by mutation and synthesis of mutant proteins that are not recognized by immune cells and antibodies. Cancerous cells are known to become resistant to certain drugs by mutations resulting in the synthesis of mutant proteins, some of which may not be recognized by the immune system. An advantage of using one of the embodiments of the present invention is that by digesting the cytosolic and/or membrane-derived proteins from cancerous cells, infected cells or pathogens, a wider range of antigenic proteins and hence a greater diversity of antigenic peptides are complexed to HSPs and/or α2M. As a result, the immune response is directed to a greater number of antigenic determinants on the antigenic cells, thus, making it more difficult for the antigenic cell, such as a cancer cell or an infected cell, to escape recognition and action by the immune system.

In another specific embodiment, the methods of the present invention generate α2M-peptide complexes that are not found naturally. α2M is an extracellular protein that is known to bind to various extracellular proteins, proteases in particular, to inactivate them and then bring them to the intracellular environment. α2M does not generally have access and therefore does not complex to the entire repertoire of antigenic peptides of an antigenic cell. The methods of the present invention allow α2M to be complexed to a much wider range of peptides that are cytosolic or membrane-derived, or that are generated by the in vitro digestion of cytosolic and membrane-derived proteins of antigenic cells.

Described in Section 4.1 are sources of antigenic cells from which protein preparations can be made. In Section 4.2, methods for making different types of protein preparations of antigenic cells and methods for digesting a protein preparation are provided. Sections 4.3 and 4.4 describes respectively the isolation or production of HSP or α2M, which are used in complexing with antigenic peptides. The in vitro complexing of HSP and antigenic peptides are described in Section 4.5. Described in Section 4.6 are methods of use of the complexes in the prevention and treatment of cancer and infectious agents, and the types of cancer and infectious diseases that are treated. The use of the compositions prepared by the methods of the invention in adoptive immunotherapy, is taught in Section 4.7. Section 5 provides experimental data showing the effectiveness of the complexes of the invention in protecting an animal prophylactically from cancer cell growth.

4.1. Sources of Antigenic Cells

The antigenic cells of the invention comprise an antigenic determinant to which an immune response in a subject is desired.

For the treatment or prevention of cancer or infectious disease, the methods of the invention provide compositions of HSPs and α2M complexed to antigenic proteins and peptides, which antigenic proteins/peptides were derived from cancer cells, preferably human cancers, e.g., fragments of tumor-specific antigens and tumor associated antigens. The peptides are generated by proteolytic digestion of proteins (e.g., cytosolic and/or membrane-derived proteins) from cancer cells, or antigenic cells that share antigenic determinants with or display similar antigenicity as the cancer cells. The antigenic peptides can also be generated by exposing the proteins to ATP, guanidium hydrochloride, and/or acidic conditions. As used herein, the term cells or tissue "of the same type of cancer" refers to cells or tissue of cancer of the same tissue type, or metastasized from cancer of the same tissue type.

For the treatment or prevention of infectious diseases, the methods of the invention provide compositions of HSPs and α2M complexed to antigenic peptides that were derived from cells infected by a pathogen or infectious agent that causes the infectious disease, or the pathogen which includes but is not limited to, a virus, bacterium, fungus, protozoan, parasite, etc. Preferably, the pathogen is one that infects humans. The antigenic peptides are generated by proteolytic digestion of (e.g., cytosolic and/or membrane-derived) proteins obtained from infected cells, antigenic cells that share antigenic determinants with or display similar antigenicity as the infected cells, or the pathogens including viral particles. The antigenic peptides can also be generated by exposing the proteins to ATP, guanidium hydrochloride, and/or acid. The antigenic peptides can also be generated from antigenic cells that display the antigenicity of an agent (pathogen) that causes the infectious disease, or a variant of such agent. In one embodiment, the population of antigenic proteins or protein preparation comprises at least 50% of the different proteins or at least 50 different proteins of cells that are transformed with a nucleic acid molecule encoding an antigen of an infectious agent, that express the antigen.

Since whole cancer cells, infected cells or other antigenic cells are used in the present methods, it is not necessary to isolate or characterize or even know the identities of these antigenic peptides in advance of using the present methods. The source of the antigenic cells may be selected, depending on the nature of the disease with which the antigens are associated. In one embodiment of the invention, any tissues, or cells isolated from a cancer, including cancer that has metastasized to multiple sites, can be used as an antigenic cell in the present method. For example, leukemic cells circulating in blood, lymph or other body fluids can also be used, solid tumor tissue (e.g., primary tissue from a biopsy) can be used. As used herein, the term cancer cell also encompasses a preneoplastic cell which is a cell in transition from a normal to a neoplastic form. The transition from non-neoplastic cell growth to neoplasia commonly consists of hyperplasia, metaplasia, and dysplasia (for review of such abnormal growth conditions (See Robbins and Angell, 1976, *Basic Pathology*, 2d Ed., W. B. Saunders Co., Philadelphia, pp. 68-79). A non-limiting list of cancers, the cells of which can be used herein is provided in Section 4.5.2 below.

In another embodiment of the invention, any cell that is infected with a pathogen or infectious agent, i.e., an infected cell, can be used as an antigenic cell for the preparation of antigenic peptides. In particular, cells infected by an intracellular pathogen, such as a virus, bacterium, fungus, parasite, or protozoan, is preferred. An exemplary list of infectious agents that can infect cells which can be used herein is provided in Section 4.5.1.

In yet another embodiment, any pathogen or infectious agent that can cause an infectious disease can be used as antigenic cell for the preparation of antigenic peptides. Variants of a pathogen or infectious agent, such as but limited to replication-defective variants, non-pathogenic or attenuated variants, non-infectious variants, can also be used as an antigenic cell for this purpose. For example, many viruses, bacteria, fungi, parasites and protozoans that can be cultured in vitro or isolated from infected materials can serve as a source of antigenic cells. Methods known in the art for propagating such pathogens including viral particles can be used.

Cell lines derived from cancer tissues, cancer cells, or infected cells can also be used as antigenic cells. Cancer or infected tissues, cells, or cell lines of human origin are preferred. Cancer cells, infected cells, or antigenic cells can be identified and isolated by any method known in the art. For example, cancer cells or infected cells can be identified by morphology, enzyme assays, proliferation assays, or the presence of pathogens or cancer-causing viruses. If the characteristics of the antigens of interest are known, antigenic cells can also be identified or isolated by any biochemical or immunological methods known in the art. For example, cancer cells or infected cells can be isolated by surgery, endoscopy, other biopsy techniques, affinity chromatography, and fluorescence activated cell sorting (e.g., with fluorescently tagged antibody against an antigen express by the cells). Antigenic cells that display similar antigenicity have one or more antigenic determinants in common against which an immune response in a subject is desired (e.g., for therapeutic or prophylactic purposes).

If the number of antigenic cells obtained from a subject is insufficient, the cells may be cultured in vitro by standard methods to expand the number of cells prior to use in the present methods. There is no requirement that a clonal or homogeneous or purified population of antigenic cells be used. A mixture of cells can be used provided that a substantial number of cells in the mixture contain the antigens of interest. In a specific embodiment, the antigenic cells and/or immune cells are purified.

In order to prepare pathogen-infected cells, uninfected cells of a cell type susceptible to infection by the pathogen or infectious agent that causes the disease can be infected in vitro. Depending on the mode of transmission and the biology of the pathogen or infectious agent, standard techniques can be used to facilitate infection by the pathogen or infectious agent, and propagation of the infected cells. For example, influenza viruses may be used to infect normal human fibroblasts; and mycobacteria may be used to infect normal human Schwann cells. In various embodiments, variants of an infectious agent, such as replication-defective viruses, non-pathogenic or attenuated mutants, or temperature-sensitive mutants can also be used to infect or transform cells to generate antigenic cells for the preparation of antigenic peptides. If large numbers of a pathogen are needed to infect cells, or if pathogens are used directly as antigenic cells, any method known in the art can be used to propagate and grow the pathogens. Such methods will depend on the pathogen, and may not involve infecting a host. For example, many techniques are known in the art for growing pathogenic bacteria, fungi and other non-viral microorganisms in culture, including large scale fermentation.

Alternatively, if the gene encoding a tumor antigen (e.g., tumor-specific antigen and tumor-associated antigen) or antigen of the pathogen is available, normal cells of the appropriate cell type from the intended recipient may be transformed or transfected in vitro with an expression construct comprising a nucleic acid molecule encoding such antigen, such that the antigen is expressed in the recipient's cells. In one embodiment, a tumor-associated antigen is an antigen that is expressed at a higher level in a tumor cell relative to a normal cell; a tumor-specific antigen is an antigen that is expressed only in a tumor cell and not in a normal cell. Optionally, more than one such antigen may be expressed in the recipient's cell in this fashion, as will be appreciated by those skilled in the art, any techniques known, such as those described in Ausubel et al. (1989, Current Protocols in Molecular Biology, Wiley Interscience), may be used to perform the transformation or transfection and subsequent recombinant expression of the antigen gene in recipient's cells.

Suitable proteins and peptides that may be expressed in such cells include, but are not limited to those displaying the antigenicity of (for the treatment or prevention of cancer): tumor antigens including tyrosinase, gp100, melan-A, gp75, mucins; and (for the treatment or prevention of infectious disease): viral proteins including proteins of immunodeficiency virus type I (HIV-I), human immunodeficiency virus type II (HIV-II), hepatitis type A, hepatitis type B, hepatitis type C, influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus and polio virus, as well as proteins or protein fragments of infectious agents including, but not limited to, mycobacteria, *rickettsia, mycoplasma, neisseria*, legionella, *leishmania,* kokzidioa, *trypanosoma, chlamydia* and *rickettsia.*

4.2. Preparation of Antigenic Proteins and Peptides

According to the invention, the compositions of the invention comprise antigenic proteins complexed to HSPs, wherein the antigenic proteins are from a preparation of proteins of the antigenic cells of interest. The compositions of the invention also comprise antigenic proteins complexed to α2M, wherein the antigenic proteins are from a preparation of proteins of the antigenic cells of interest. The compositions of the invention also comprise complexes of HSPs and antigenic peptides, or complexes of α2M and antigenic peptides that are prepared by first, generating a population of peptides from a preparation of proteins of the antigenic cells of interest, and then complexing the peptides to HSPs or α2M.

In various embodiments, to maximize and preserve the diversity of antigenic proteins and peptides, the methods used for preparing a protein preparation of antigenic cells do not selectively remove or retain any particular protein or peptide from other proteins and peptides in the antigenic cell. Even in certain embodiments when cytosolic proteins or membrane-derived proteins are used, the methods used to make the preparations do not selectively remove or retain any particular protein of the cytosol or of the membranes. Therefore, the majority of the proteins present in the cytosol or in the membranes are also present in the respective preparations of antigenic proteins and peptides from antigenic cells. In preferred embodiments, substantially the entire repertoire of antigenic proteins and peptides of the antigenic cells, and substantially all the antigenic proteins and peptides in the cytosol or in the membranes are present in the complexing reaction and form complexes with HSPs and/or α2M.

4.2.1 Protein Preparations of Antigenic Cells

In one embodiment of the invention, a protein preparation is provided which is derived from a cancer cell, infected cell, or pathogen. For example, for the treatment of cancer, the protein preparations are prepared, postoperatively, from tumor cells obtained from a cancer patient. In another embodiment of the present invention, one or more antigenic proteins of interest are synthesized in cell lines modified by the introduction of recombinant expression systems that encode such antigens, and such cells are used to prepare the proteins. The proteins can be obtained from one or more cellular fraction(s), for example, the cytosol-of the antigenic cells, or they can be extracted or solubilized from the membranes or cell walls of the antigenic cells. Any technique known in the art for cell lysis, fractionation of cellular contents, and protein enrichment or isolation can be used. See, for example, Current Protocols in Immunology, vol. 2, chapter 8, Coligan et al. (ed.), John Wiley & Sons, Inc.; Pathogenic and Clinical Microbiology: A Laboratory Manual by Rowland et al., Little Brown & Co., June 1994; which are incorporated herein by reference in their entireties. Depending on the techniques used to fractionate the cellular contents, a cellular fraction comprises at least 20, 50, 100, 500, 1,000, 5,000, 10,000, or 20,000 different proteins.

As used herein, the term "protein preparation" refers to a mixture of proteins obtained from antigenic cells, a cellular fraction of antigenic cells, or virus particles. The proteins can be obtained from a cellular fraction, such as the cytosol. The proteins can also be non-cytosolic proteins (e.g., those from cell walls, cell membranes or organelles), or both. Cellular fractions may include but are not limited to cytosolic fractions, membrane fractions, and organelle fractions, such as nuclear, mitochondrial, lysosomal, and endoplasmic reticulum-derived fractions. The protein preparations can be obtained from non-recombinant or recombinant cells. The term "antigenic proteins" as used herein also encompasses antigenic polypeptides and antigenic peptides that may be present in the preparation. The protein preparation obtained from the antigenic cells or cellular fractions thereof or virus particles can optionally be purified from other non-proteinaceous materials to various degrees by techniques known in the art. The protein preparation may comprise at least 50%, 55%, 60%, 65%, 70%, 75%, 80%, 85%, 90%, 95% 97%, 98%, 99% of the different proteins and peptides present in the antigenic cells or virus particles or a fraction of the antigenic cells.

In a specific embodiment, the protein preparations have not been subjected to any method of preparation that selectively removes or retains one or more particular protein(s) from the other proteins in the antigenic cells.

In a specific embodiment, the protein preparation is the total cell lysate which is not fractionated and/or purified, and may contain other non-proteinaceous materials of the cells. In another specific embodiment, the protein preparation is total protein in a cellular fraction, which has not been subjected to further fractionation or purification, and may contain other non-proteinaceous materials of the cells. In yet another embodiment, the protein preparation is the total protein in a preparation of viral particles. In specific embodiments, the protein preparation comprises total cellular protein, total cytosolic proteins, or total membrane-bound proteins of antigenic cell(s). In various embodiments, the protein preparation comprises at least 20, 50, 100, 500, 1,000, 5,000, 10,000, or 20,000 different proteins. A plurality of different antigenic proteins are present in a protein preparation of antigenic cells. Moreover, the proteins in the protein preparation may be subjected to a step of protease digestion prior to in vitro complexing to HSPs or α2M. Alternatively, the proteins in the protein preparation are not subjected to a step of protease digestion prior to in vitro complexing to HSPs or α2M.

To make a protein preparation of antigenic cells or virus particles, the lysing of antigenic cells or disruption of cell walls, cell membranes, or viral particle structure can be performed using standard protocols known in the art. In various embodiments, the antigenic cells can be lysed, for example, by mechanical shearing, sonication, freezing and thawing, adjusting the osmolarity of the medium surrounding the cells, or a combination of techniques. In less preferred embodiments, the antigenic cells can be lysed by chemicals, such as detergents.

Once the cells are lysed, it is desirable to remove cellular debris, materials that are non-proteinaceous or materials that do not contain cytosolic, and/or membrane-derived proteins (including proteins in the membranes of organelles). Removal of these components can be accomplished by techniques such as low speed centrifugation or filtration. After removing cellular debris and intact cells, a high speed centrifugation step can be used to separate the cytosolic proteins which are in the supernatant, and the membrane-derived proteins which are collected in the pellet. Standard procedures commonly known in the art allows the further isolation of the membrane-derived proteins from the pellet. Standard techniques commonly known in the art can be used to extract viral proteins from viral particles. In certain embodiments, the methods used do not or are not designed to selectively remove or retain any one or more particular protein(s) from other proteins that are present in the antigenic cell, in the cytosol or in the membranes.

In other embodiments, optionally, the proteins from the antigenic cells can be separated by their general biochemical and/or biophysical properties, such as size, charge, or combinations thereof. Any techniques known in the art can be used to perform the separation. Selected fractions of the proteins/peptides that comprise at least 20, 50, 100, 500, 1,000, 5,000, 10,000, or 20,000 different proteins or that comprise at least 50%, 55%, 60%, 65%, 70%, 75%, 80%, 85%, 90%, 95% 97%, 98%, 99% of the different proteins present in the antigenic cells or a cellular fraction thereof, or virus particles, are used to form complexes to HSP or α2M.

An exemplary, but not limiting, method that may be used to make a protein preparation comprising cytosolic proteins is as follows:

Cells, which may be tumor cells derived from a biopsy of the patient or tumor cells cultivated in vitro, or cell infected with a pathogenic agent, are suspended in 3 volumes of 1×Lysis buffer comprising 30 mM sodium bicarbonate pH 7.5, 1 mM PMSF, incubated on ice for 20 minutes and then the hypotonically-swollen cells are homogenized in a dounce homogenizer until >95% cells are lysed. As an alternative to shearing, cells can be sonicated, on ice, until >99% cells are lysed as determined by microscopic examination. When sonication is used, cells are suspended in a buffer such as phosphate buffered saline (PBS) which may comprises 1 mM PMSF, before sonication.

The lysate is centrifuged at 1,000×g for 10 minutes to remove intact cells, nuclei and other cellular debris. The resulting supernatant is recentrifuged at about 100,000×g for about one hour, and the supernatant recovered. The 100,000×g supernatant may be dialyzed for 36 hours at 4° C. (three times, 100 times volumes each time) against PBS or other suitable buffer, to provide the soluble cytosolic proteins of the present invention. If necessary, insoluble material in the preparation may be removed by filtration or low-speed centrifugation.

An exemplary, but not limiting, method that may be used to make a protein preparation comprising membrane-derived proteins is as follows:

Cells, which may be tumor cells derived from a biopsy of the patient or tumor cells cultivated in vitro, or cells infected with a pathogenic agent, are suspended in 3 volumes of 1×Lysis buffer comprising 30 mM sodium bicarbonate pH 7.5, 1 mM PMSF, incubated on ice for 20 minutes and then the hypotonically-swollen cells are homogenized in a dounce homogenizer until >95% cells are lysed. As an alternative to shearing, cells can be sonicated, on ice, until >99% cells are lysed as determined by microscopic examination. When sonication is used, cells are suspended in a buffer such as phosphate buffered saline (PBS) which may comprises 1 mM PMSF, before sonication.

The lysate is then centrifuged at 100,000×g for 10 minutes to collect the cell membranes. Membrane-derived proteins can be dislodged from the lipid bilayer and isolated from the 100,000 g pellet (where the membrane-derived proteins are located) by resuspending the pellet in 5 volumes of PBS containing 1% sodium deoxycholate (without $Ca^{2+}$ and $Mg^{2+}$) and incubated on ice for 1 h. The resulting suspension is centrifuged for 30 min at 20,000 g and the resulting supernatant harvested and dialyzed against several changes of PBS (without $Ca^{2+}$ and $Mg^{2+}$) to remove the detergent. The resulting dialysate is centrifuged for 90 min at 100,000 g and the supernatant purified further. Then calcium and magnesium are both added to the supernatant to give final concentrations of 2 mM. If necessary, insoluble material in the preparation may be removed by filtration or low-speed centrifugation.

In a specific embodiment, the population of cytosolic and/or membrane-derived proteins obtained from antigenic cells can be complexed to HSP or α2M directly without protease treatment or any further extraction or selection processes. Alternatively, the proteins can be subjected to protease treatment prior to complexing.

4.2.2 Peptides from Antigenic Cells

According to the invention, the cytosolic and membrane-derived proteins obtained from antigenic cells can be optionally digested to generate antigenic peptides. In one embodiment, either the cytosolic or the membrane-derived proteins are used in the digestion. In another embodiment, the cytosolic and membrane-derived proteins are combined in the digestion reaction to generate antigenic peptides. In preferred embodiments, the protein preparations that are used in the protease digestion have not been subjected to any method(s) of preparation that selectively remove or retain one or more particular protein(s) from the other proteins in the antigenic cells, or the cytosol or membranes of the antigenic cells.

Various proteases or proteolytic enzymes can be used in the invention to produce from a protein preparation of antigenic cells a population of peptides which comprises antigenic peptides. The enzymatic digestions can be performed either individually or in suitable combinations with any of the proteolytic enzymes that are well known in the art including, but not limited to, trypsin, Staphylococcal peptidase I (also known as protease V8), chymotrypsin, pepsin, cathepsin G, thermolysin, elastase, and papain. Trypsin is a highly specific serine proteinase that cleaves on the carboxyl-terminal side of lysines and arginines. Due to the limited number of cleavage sites, it is expected to leave many MHC-binding epitopes intact. Staphylococcal peptidase I, a serine proteinase, has specificity for cleavage after glutamic and aspartic acid residues. A digestion can be carried out with a single protease or a mixture of proteases. The proteases or proteolytic enzymes used are incubated under conditions suitable for the particular enzyme. Preferably, the enzyme is purified. Non-enzymatic methods, such as cyanogen bromide cleavage, can also be used for generating peptides. The protein preparation to be digested can be aliquoted into a plurality of reactions each using a different enzyme, and the resulting peptides may optionally be pooled together for use. It may not be necessary to completely digest the proteins in the enzymatic reactions. These reactions results in the generation of a diverse and different set of peptides for each protein that is present in the protein preparation. The production of different peptide sets allows for a greater probability of generating antigenic peptides that are capable of inducing an immune response to the antigens in the protein preparation when they are complexed to HSP or α2M. In a preferred embodiment, the protein preparation to be digested is aliquoted into two separate reactions and two different proteolytic enzymes are used to produce two different sets of peptides of the proteins present in the protein preparation. Depending on the proteins, enzymes and reaction conditions, undigested proteins may remain in the reactions. In a preferred embodiment, trypsin and Staphylococcal peptidase I are used separately to digest the protein preparation.

In another preferred embodiment, the proteolytic enzymes used in the invention exhibit similar activities as the proteolytic activities that are found in the proteasome. The proteasome is responsible for the extralysosomal, endocatalytic degradation of cytosolic and nuclear proteins which are misfolded or damaged in a cell. The proteasome can degrade proteins completely to yield single amino acids, can generate optimal major histocompatibility complex class I (MHC I)-binding epitopes, and can generate longer peptide precursors which could potentially undergo further trimming elsewhere in the cell to yield cytotoxic T cell epitopes. Cleavage preferences of the proteasome is on the carboxyl (COOH)-side of basic, acidic, and hydrophobic amino acids. Three known proteolytic enzymatic activities that are present in the proteasome are chymotrypsin-like activity, trypsin-like activity, and peptidylglutamylpeptide-hydrolyzing activity (Uebel and Tampe, 1999, Curr. Opin. Immunol. 11:2 203-208). As such, enzymes having such activities and specificities can be used separately or in combination to digest the protein preparation. In a preferred embodiment, trypsin, chymotrypsin, and/or peptidylglutamylpeptide-hydrolase are used.

The resulting peptide digestions comprise antigenic peptides, non-antigenic peptides, and single amino acid residues. The reactions may also comprise undigested or incompletely digested antigenic proteins. The proteolytic enzymatic digestions of the invention are monitored in order to generate peptides that fall within a desirable range of lengths. In a preferred embodiment, the peptides generated are from about 7 to about 20 amino acid residues. Most antigenic peptides that are presented to T cells by MHC class I and class II fall within this range. In various embodiments, the population of peptides comprises peptides having a size range of 6 to 21, 8 to 19, 10 to 20, or at least 7, 8, 9, 10, 11, 12, 15, 20, 25, 30, 40, 45, or 50, amino acid residues. In preferred embodiments, the antigenic peptides have 7, 8, 9, 10, 11, 12, 13, 14, 15, 16, 17, 18, 19, or 20 amino acid residues. To monitor the progression of protein digestion, a test reaction can be performed where small aliquots of a protein digestion are taken out of the reaction and monitored for the progression of digestion through either tricine-polyacrylamide gel electrophoresis ("tricine-PAGE"), high performance liquid chromatography ("HPLC"), or mass spectrometry, or any other method known in the art to determine the size of peptides. Using such a test reaction, a determination can be made as to when peptide fragments of a particular size range will be generated at a particular enzymatic concentration. Other variables of the reaction that can be manipulated include the amount of protein in the reaction, the temperature, the duration of incubation, the presence of cofactors, etc.

Once the proper conditions are established for the generation of peptide fragments of a particular size range from a type of antigenic cell, the enzymatic reaction conditions can be duplicated to generate antigenic peptides which can be pooled. It is preferred that the enzymatic digestion is terminated before the peptides are complexed to HSPs or α2M. In one embodiment of the invention, inhibitors can be used for terminating an enzymatic digestion. Enzymatic inhibitors that can be used in the invention include, but are not limited to, PMSF, bestatin, amastatin, leupeptin, and cystatin, depending on which enzymes are used in the protein digestion. Inhibitors for most proteases are well known in the art. Alternatively, another method of terminating an enzymatic digestion is by physical removal of the enzyme from the reaction. This can be done by attaching the enzyme of choice to a solid phase, such as a resin or a material that can easily be removed from the reaction by well known methods such as centrifugation or filtration. The protein preparation is allowed to contact or flow across the solid phase for a period of time. Such immobilized enzymes can be purchased commercially or can be produced by procedures for immobilizing enzymes that are well known in the art.

At the end of the digestion reaction, the peptides can optionally be separated from low molecular weight materials, such as dipeptides, or single amino acid residues, in the preparation. For example, the peptides can be isolated by centrifugation through a membrane, such as the Centriprep-3. Optionally, the peptides can be separated by their general biochemical and/or biophysical properties, such as size, charge, or combinations thereof. Any techniques known in the art can be used to perform the separation resulting in digested protein preparation comprising at least 50, 100, 500, 1,000, 5,000, 10,000, 20,000, 50,000, or 100,000 different peptides.

In another embodiment of the invention, peptides that are endogenously present in antigenic cells can be used in the invention either alone or in combination with the peptides generated by the proteolytic digestion of the cytosolic and membrane-derived proteins. Peptides that are endogenously present in antigenic cells include peptides that are complexed in vivo to HSP and/or MHC class I and II molecules. According to the invention, such peptides that are isolated directly from a protein preparation of antigenic cells can be complexed to HSPs and/or α2M.

In specific embodiments, either the cytosolic or the membrane-derived proteins are used in the isolation process. In another specific embodiment, the cytosolic and membrane-derived proteins are combined in the isolation process. In preferred embodiments, the protein preparations that are used in the isolation have not been subjected to any method(s) of preparation that selectively remove or retain one or more particular protein(s) from the other proteins in the antigenic cells, or the cytosol or membranes of the antigenic cells. The antigenic peptides are isolated directly from a protein preparation of the cell without isolating complexes of antigenic peptides and HSP or MHC molecules first. Preferably, the protein preparation comprises comprise at least 20, 50, 100, 500, 1,000, 5,000, 10,000, or 20,000 different proteins or that comprise at least 50%, 55%, 60%, 65%, 70%, 75%, 80%, 85%, 90%, 95% 97%, 98%, 99% of the different proteins present in the antigenic cells or a cellular fraction thereof, or virus particles.

In various embodiments, the method comprise treating the protein preparation to ATP, guanidium hydrochloride, and/or exposing the protein preparation to acidic conditions such that antigenic peptides that are associated with proteins such as HSPs and MHC class I and II molecules in the protein preparation can be eluted. Many different acids can be used, including but not limited to, trifluoroacetic acid. Methods are known in the art for the isolation of peptides from HSP-peptide complexes, such as Menoret et al., 1999, Biochem. Biophys. Res. Commun. 262(3):813-8, which is incorporated herein by reference in its entirety. Methods known in the art such as those described in Marston and Hartley (1990, Meth. Enzymol. 182:264-276) for dissociating protein aggregates can also be used.

In particular, the isolation process comprises exposing a protein preparation of antigenic cells with ATP, for example, at room temperature for one hour, and/or treating a protein preparation of antigenic cells with trifluoroacetic acid (TFA), for example 0.1% TFA. The treatment preferably comprises sonicating the protein preparation in 0.1% TFA. In a most preferred embodiment, a protein preparation is first exposed to ATP, followed by sonication in 0.1% TFA. Various protease inhibitors can be used in the invention prior to cell lysis and the isolation process to prevent or reduce cleavage of cellular protein that may generate peptides that are not endogenously associated with HSPs or α2M. For example, a mixture of 14 protease inhibitors can be used: phenylmethylsulfonyl fluoride (PMSF) 2 mM, ethylenediaminetetreacedic acid (EDTA) 1 mM, ethylene glycolbis(P-aminoethyl ether)N,N,N',N'-tetraacetic acid (EGTA) 1 mM, (all obtained from Sigma, St. Louis, Mo.), and Antipain 20 mg/ml, Bestatin 5 mg/ml, Chemostatin 20 ptg/ml, E64 20 μg/ml, Leupeptine 1 ttg/ml, Pepstatine 1 gg/ml, Pefabloc 40 Ag/ml, and Apoprotein 10 tkg/ml (all obtained from Boehringer Mannheim, Indianapolis, Ind.). The peptides resulting from the protein preparation comprise antigenic peptides and non-antigenic peptides of a variety of sizes ranging from at least 7, 8, 9, 10, 11, 12, 15, 20, 25, 30, 40, 45, or 50, amino acid residues. At the end of the process, the peptides are preferably recovered by separating from the proteins in the preparation prior to complexing with HSP or α2M. For example, the peptides can be recovered by centrifugation through a membrane, such as the Centriprep-3, by drying under vacuum, or by reverse phase chromatography, e.g., fractionation in a BioCad20 microanalytiocal HPLC Poros RH2 column (Perseptive Biosystems, Cambridge, Mass.), equilibrated with 0.1% TFA in water and elution by acetonitrile. Accordingly, antigenic peptides that are endogenously present in antigenic cells and that are isolated directly from a protein preparation can be complexed to HSPs and/or α2M. Alternatively, a mixed population of peptides comprising peptides that are endogenously present in antigenic cells and peptides from digested cytosolic and membrane-derived proteins, can be complexed to HSPs and/or α2M.

4.3. Preparation of HSPs and α2M

According to the present invention, antigenic peptides derived from antigenic cells are complexed to HSPs and/or α2M. Described herein are exemplary methods that can be used for isolating and preparing HSPs and α2M for use in the invention.

Heat shock proteins, which are also referred to interchangeably herein as stress proteins, useful in the practice of the instant invention can be selected from among any cellular protein that satisfies the following criteria. It is a protein whose intracellular concentration increases when a cell is exposed to a stressful stimuli, it is capable of binding other proteins or peptides, it is capable of releasing the bound proteins or peptides in the presence of adenosine triphosphate (ATP) or under acidic conditions; and it is a protein showing at least 35% homology with any cellular protein having the above properties.

The first stress proteins to be identified were the heat shock proteins (HSPs). As their name implies, HSPs are synthesized by a cell in response to heat shock. To date, five major classes of HSPs have been identified, based on the molecular weight of the family members. These classes are called sHSPs (small heat shock proteins), HSP60, HSP70, HSP90, and HSP 100, where the numbers reflect the approximate molecular weight of the HSPs in kilodaltons. In addition to the major HSP families, an endoplasmic reticulum resident protein, calreticulin, has also been identified as yet another heat shock protein useful for eliciting an immune response when complexed to antigenic molecules (Basu and Srivastava, 1999, J. Exp. Med. 189:797-202). Other stress proteins that can be used in the invention include but are not limited to grp78 (or BiP), protein disulphide isomerase (PDI), HSP110, and grp170 (Lin et al., 1993, Mol. Biol. Cell, 4:1109-1119; Wang et al., 2001, J. Immunol., 165:490-497). Many members of these families were found subsequently to be induced in response to other stressful stimuli including, but not limited to, nutrient deprivation, metabolic disruption, oxygen radicals, hypoxia and infection with intracellular pathogens. (See Welch, May 1993, Scientific American 56-64; Young, 1990, Annu. Rev. Immunol. 8:401-420; Craig, 1993, Science 260:1902-1903; Gething; et al., 1992, Nature 355:33-45; and Lindquist, et al., 1988, Annu. Rev. Genetics 22:631-677), the disclosures of which are incorporated herein by reference. It is contemplated that HSPs/stress proteins belonging to all of these families can be used in the practice of the instant invention.

The major HSPs can accumulate to very high levels in stressed cells, but they occur at low to moderate levels in cells that have not been stressed. For example, the highly inducible mammalian HSP70 is hardly detectable at normal temperatures but becomes one of the most actively synthesized proteins in the cell upon heat shock (Welch, et al., 1985, J. Cell. Biol. 101:1198-1211). In contrast, HSP90 and HSP60 proteins are abundant at normal temperatures in most, but not all, mammalian cells and are further induced by heat (Lai, et al., 1984, Mol. Cell. Biol. 4:2802-10; van Bergen en Henegouwen, et al., 1987, Genes Dev. 1:525-31).

Heat shock proteins are among the most highly conserved proteins in existence. For example, DnaK, the HSP70 from E. coli has about 50% amino acid sequence identity with HSP70 proteins from excoriates (Bardwell, et al., 1984, Proc. Natl. Acad. Sci. 81:848-852). The HSP60 and HSP90 families also show similarly high levels of intrafamilies conservation (Hickey, et al., 1989, Mol. Cell. Biol. 9:2615-2626; Jindal, 1989, Mol. Cell. Biol. 9:2279-2283). In addition, it has been discovered that the HSP60, HSP70 and HSP90 families are composed of proteins that are related to the stress proteins in sequence, for example, having greater than 35% amino acid identity, but whose expression levels are not altered by stress. Therefore it is contemplated that the definition of heat shock protein or stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus.

In an embodiment wherein the HSP portion of the HSP-antigenic peptide complex is desired to be purified from cells, exemplary purification procedures such as described in Sections 4.3.1-4.3.3 below can be employed to purify HSP-peptide complexes, after which the HSPs can be separated from the endogenous HSP-peptide complexes in the presence of ATP or under acidic conditions, for subsequent in vitro complexing to a population of antigenic peptides. See Peng, et al., 1997, J. Immunol. Methods, 204:13-21; Li and Srivastava, 1993, EMBO J. 12:3143-3151, which are incorporated herein by reference in their activities. Although described for tumor cells, the protocols described hereinbelow may be used to isolate HSPs from any infected cells, and any eukaryotic cells, for example, tissues, isolated cells, or immortalized eukaryote cell lines infected with an intracellular pathogen, tumor cells or tumor cell lines.

4.3.1. Preparation and Purification of HSP70-Peptide Complexes

The purification of HSP70-peptide complexes has been described previously, see, for example, Udono et al., 1993, J. Exp. Med. 178:1391-1396. A procedure that may be used, presented by way of example but not limitation, is described below.

Initially, tumor cells are suspended in 3 volumes of 1×Lysis buffer consisting of 30 mM sodium bicarbonate pH 7.5, 1 mM PMSF. Then, the pellet is sonicated, on ice, until >99% cells are lysed as determined by microscopic examination. As an alternative to sonication, the cells may be lysed by mechanical shearing by homogenizing the cells in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose. The supernatant is then allowed to bind to the Con A Sepharose for 2-3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immuno-blotting using an appropriate anti-HSP70 antibody (such as from clone N27F3-4, from StressGen).

Fractions strongly immunoreactive with the anti-HSP70 antibody are pooled and the HSP70-peptide complexes precipitated with ammonium sulfate; specifically with a 50%-70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex® G25 column (Pharmacia). If necessary the HSP70 preparation thus obtained can be repurified through the Mono Q FPLC Column as described above.

The HSP70-peptide complex can be purified to apparent homogeneity using this method. Typically 1 mg of HSP70-peptide complex can be purified from 1 g of cells/tissue.

An improved method for purification of HSP70 comprises contacting cellular proteins with ATP or a nonhydrolyzable analog of ATP affixed to a solid substrate, such that HSP70 in the lysate can bind to the ATP or nonhydrolyzable ATP analog, and eluting the bound HSP70. A preferred method uses column chromatography with ATP affixed to a solid substratum (e.g., ATP-agarose). The resulting HSP70 preparations are higher in purity and devoid of contaminating peptides. The HSP70 yields are also increased significantly by about more than 10 fold.

Alternatively, chromatography with nonhydrolyzable analogs of ADP, instead of ATP, can be used for purification of HSP70-peptide complexes. By way of example but not limitation, purification of HSP70 free of peptide by ATP-agarose chromatography can be carried out as follows:

Meth A sarcoma cells (500 million cells) are homogenized in hypotonic buffer and the lysate is centrifuged at 100,000 g for 90 minutes at 4° C. The supernatant is applied to an ATP-agarose column. The column is washed in buffer and is eluted with 5 column volumes of 3 mM ATP. The HSP70 elutes in fractions 2 through 10 of the total 15 fractions which elute. The eluted fractions are analyzed by SDS-PAGE. The HSP70 can be purified to apparent homogeneity using this procedure.

4.3.2. Preparation and Purification of HSP90-Peptide Complexes

A procedure that can be used, presented by way of example but not limitation, is described below.

Initially, tumor cells are suspended in 3 volumes of 1×Lysis buffer consisting of 30 mM sodium bicarbonate pH 7.5, 1 mM PMSF. Then, the pellet is sonicated, on ice, until >99% cells are lysed as determined by microscopic examination. As an alternative to sonication, the cells may be lysed by mechanical shearing by homogenizing the cells in a Dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2×Lysis buffer prior to mixing with Con A Sepharose. The supernatant is then allowed to bind to the Con A Sepharose for 2-3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated with lysis buffer. The proteins are then eluted with a salt gradient of 200 mM to 600 mM NaCl.

The eluted fractions are fractionated by SDS-PAGE and fractions containing the HSP90-peptide complexes identified by immunoblotting using an anti-HSP90 antibody such as 3G3 (Affinity Bioreagents). HSP90-peptide complexes can be purified to apparent homogeneity using this procedure. Typically, 150-200 µg of HSP90-peptide complex can be purified from Ig of cells/tissue.

4.3.3. Preparation and Purification of GP96-Peptide Complexes

A procedure that can be used, presented by way of example but not limitation, is described below.

A pellet of tumors is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cell type) on ice until >95% cells are lysed.

The lysate is centrifuged at 1,000 g for 10 minutes to remove unbroken cells, nuclei and other debris. The supernatant from this centrifugation step is then recentrifuged at 100,000 g for 90 minutes. The gp96-peptide complex can be purified either from the 100,000 pellet or from the supernatant.

When purified from the supernatant, the supernatant is diluted with equal volume of 2×lysis buffer and the supernatant mixed for 2-3 hours at 4° C. with Con A Sepharose equilibrated with PBS containing 2 mM $Ca^{2+}$ and 2 mM $Mg^{2+}$. Then, the slurry is packed into a column and washed with 1×lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60-95% pure, however this depends upon the cell type and the tissue-to-lysis buffer ratio used. Then the sample is applied to a Mono Q FPLC column (Pharmacia) equilibrated with a buffer containing 5 mM sodium phosphate, pH 7. The proteins are then eluted from the column with a 0-1 M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose purification after the Con A purification step but before the Mono Q FPLC step.

In the first optional step, described by way of example as follows, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose and the procedure followed as before.

In the second optional step, described by way of example as follows, the gp96 containing fractions eluted from the Con A column are pooled and the buffer exchanged for 5 mM sodium phosphate buffer, pH 7, 300 mM NaCl by dialysis, or preferably by buffer exchange on a Sephadex G25 column. After buffer exchange, the solution is mixed with DEAE-Sepharose previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 nm drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q FPLC column (Pharmacia) equilibrated with 5 mM sodium phosphate buffer, pH 7 and the protein that binds to the Mono Q FPLC column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10-20 µg of gp96 can be isolated from 1 g cells/tissue.

4.3.4. Preparation and Purification of α2M

Alpha-2-macroglobulin can be bought from commercial sources or prepared by purifying it from human blood. To purify α2M from blood, the following non-limiting protocol can be used by way of example:

Blood is collected from a subject and is allowed to clot. It is then centrifuged for 30 minutes under 14,000×g to obtain the serum which is then applied to a gel filtration column (Sephacryl S-300R) equilibrated with 0.04M Tris buffer pH 7.6 plus 0.3M NaCl. A 65 ml column is used for about 10 ml of serum. Three ml fractions are collected and each fraction is tested for the presence of α2M by dot blot using an α2M specific antibody. The α2M positive fractions are pooled and applied to a PD10 column to exchange the buffer to 0.01M Sodium Phosphate buffer pH 7.5 with PMSF. The pooled fractions are then applied to a Con A column (10 ml) equilibrated with the phosphate buffer. The column is washed and the protein is eluted with 5% methylmannose pyranoside. The eluent is passed over a PD10 column to change the buffer to a Sodium Acetate buffer (0.05 M; pH 6.0). A DEAE column is then equilibrated with acetate buffer and the sample is applied to the DEAE column. The column is washed and the protein is eluted with 0.13M sodium acetate. The fractions with α2M are then pooled. The α2M can be purified to apparent homogeneity using this procedure as assayed by sodium dodecyl sulfate-polyacrylamide gel electrophoresis.

4.3.5. Recombinant Expression of Heat Shock Proteins And α2M

In certain embodiments of the present invention, HSPs and α2M can be prepared from cells that express higher levels of HSPs and α2M through recombinant means. Amino acid sequences and nucleotide sequences of many HSPs and α2M are generally available in sequence databases, such as GenBank. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics. Such nucleotide sequences of non-limiting examples of HSPs that can be used for the compositions, methods, and for preparation of the HSP peptide-complexes of the invention are as follows: human HSP70, Genbank Accession No. M24743, Hunt et al., 1995, Proc. Natl. Acad. Sci. U.S.A., 82: 6455-6489; human HSP90, Genbank Accession No. X15183, Yamazaki et al., Nucl. Acids Res. 17: 7108; human gp96: Genbank Accession No. X15187, Maki et al., 1990, Proc. Natl. Acad. Sci. U.S.A. 87: 5658-5562; human BiP: Genbank Accession No. M19645; Ting et al., 1988, DNA 7: 275-286; human HSP27, Genbank Accession No. M24743; Hickey et al., 1986, Nucleic Acids Res. 14: 4127-45; mouse HSP70: Genbank Accession No. M35021, Hunt et al., 1990, Gene 87: 199-204; mouse gp96: Genbank Accession No. M16370, Srivastava et al., 1987, Proc. Natl. Acad. Sci. U.S.A. 85: 3807-3811; and mouse BiP: Genbank Accession No. U16277, Haas et al., 1988, Proc. Natl. Acad. Sci. U.S.A. 85: 2250-2254. Degenerate sequences encoding HSPs can also be used.

As used herein, the term "α2M" embraces other polypeptide fragments, analogs, and variants of α2M having at least 35% to 55%, preferably 55% to 75%, and most preferably 75% to 85% amino acid identity with α2M, and is capable of forming a complex with an antigenic peptide, which complex is capable of being taken up by an antigen presenting cell and eliciting an immune response against the antigenic molecule. The α2M molecule of the invention can be purchased commercially or purified from natural sources (Kurecki et al., 1979, Anal. Biochem. 99:415-420), chemically synthesized, or recombinantly produced. Non-limiting examples of α2M sequences that can be used for preparation of the α2M polypeptides of the invention are as follows: Genbank Accession Nos. M11313, P01023, AAA51551; Kan et al., 1985, Proc. Nat. Acad. Sci. 82: 2282-2286. A degenerate sequence encoding α2M can also be used.

Once the nucleotide sequence encoding the HSP or α2M of choice has been identified, the nucleotide sequence, or a fragment thereof, can be obtained and cloned into an expression vector for recombinant expression. The expression vector can then be introduced into a host cell for propagation of the HSP or α2M. Methods for recombinant production of HSPs or α2M are described in detail herein.

The DNA may be obtained by DNA amplification or molecular cloning directly from a tissue, cell culture, or cloned DNA (e.g., a DNA "library") using standard molecular biology techniques (see e.g., Methods in Enzymology, 1987, volume 154, Academic Press; Sambrook et al. 1989, Molecular Cloning—A Laboratory Manual, 2nd Edition, Cold Spring Harbor Press, New York; and Current Protocols in Molecular Biology, Ausubel et al. (eds.), Greene Publishing Associates and Wiley Interscience, New York, each of which is incorporated herein by reference in its entirety). Clones derived from genomic DNA may contain regulatory and intron DNA regions in addition to coding regions; clones derived from cDNA will contain only exon sequences. Whatever the source, the HSP or α2M gene should be cloned into a suitable vector for propagation of the gene.

In a preferred embodiment, DNA can be amplified from genomic or cDNA by polymerase chain reaction (PCR) amplification using primers designed from the known sequence of a related or homologous HSP or α2M. PCR is used to amplify the desired sequence in DNA clone or a genomic or cDNA library, prior to selection. PCR can be carried out, e.g., by use of a thermal cycler and Taq polymerase (Gene Amp®). The polymerase chain reaction (PCR) is commonly used for obtaining genes or gene fragments of interest. For example, a nucleotide sequence encoding an HSP or α2M of any desired length can be generated using PCR primers that flank the nucleotide sequence encoding open reading fram. Alternatively, an HSP or α2M gene sequence can be cleaved at appropriate sites with restriction endonuclease(s) if such sites are available, releasing a fragment of DNA encoding the HSP or α2M gene. If convenient restriction sites are not available, they may be created in the appropriate positions by site-directed mutagenesis and/or DNA amplification methods known in the art (see, for example, Shankarappa et al., 1992, PCR Method Appl. 1: 277-278). The DNA fragment that encodes the HSP or α2M is then isolated, and ligated into an appropriate expression vector, care being taken to ensure that the proper translation reading frame is maintained.

In an alternative embodiment, for the molecular cloning of an HSP or α2M gene from genomic DNA, DNA fragments are generated to form a genomic library. Since some of the sequences encoding related HSPs or α2M are available and can be purified and labeled, the cloned DNA fragments in the genomic DNA library may be screened by nucleic acid hybridization to a labeled probe (Benton and Davis, 1977, Science 196: 180; Grunstein and Hogness, 1975, Proc. Natl. Acad. Sci. U.S.A. 72: 3961). Those DNA fragments with substantial homology to the probe will hybridize. It is also possible to identify an appropriate fragment by restriction enzyme digestion(s) and comparison of fragment sizes with those expected according to a known restriction map.

Alternatives to isolating the HSP or α2M genomic DNA include, but are not limited to, chemically synthesizing the gene sequence itself from a known sequence or synthesizing a cDNA to the mRNA which encodes the HSP or α2M. For example, RNA for cDNA cloning of the HSP or α2M gene can be isolated from cells which express the HSP or α2M. A cDNA library may be generated by methods known in the art and screened by methods, such as those disclosed for screening a genomic DNA library. If an antibody to the HSP or α2M is available, the HSP or α2M may be identified by binding of a labeled antibody to the HSP- or α2M-synthesizing clones.

Other specific embodiments for the cloning of a nucleotide sequence encoding an HSP or α2M, are presented as examples but not by way of limitation, as follows: In a specific embodiment, nucleotide sequences encoding an HSP or α2M can be identified and obtained by hybridization with a probe comprising a nucleotide sequence encoding HSP or α2M under various conditions of stringency which are well known in the art (including those employed for cross-species hybridizations).

Any technique for mutagenesis known in the art can be used to modify individual nucleotides in a DNA sequence, for purpose of making amino acid substitution(s) in the expressed peptide sequence, or for creating/deleting restriction sites to facilitate further manipulations. Such techniques include but are not limited to, chemical mutagenesis, in vitro site-directed mutagenesis (Hutchinson et al., 1978, J. Biol. Chem. 253: 6551), oligonucleotide-directed mutagenesis (Smith, 1985, Ann. Rev. Genet. 19: 423-463; Hill et al., 1987, Methods Enzymol. 155: 558-568), PCR-based overlap extension (Ho et al., 1989, Gene 77: 51-59), PCR-based megaprimer mutagenesis (Sarkar et al., 1990, Biotechniques 8: 404-407), etc. Modifications can be confirmed by double stranded dideoxynucleotide DNA sequencing.

In certain embodiments, a nucleic acid encoding a secretory form of a non-secreted HSP is used to practice the methods of the present invention. Such a nucleic acid can be constructed by deleting the coding sequence for the ER retention signal, KDEL. Optionally, the KDEL coding sequence is replaced with a molecular tag to facilitate the recognition and purification of the HSP, such as the Fc portion of murine IgG1. In another embodiment, a molecular tag can be added to naturally secreted HSPs or α2M. PCT publication no. WO 99/42121 demonstrates that deletion of the ER retention signal of gp96 resulted in the secretion of gp96-Ig peptide-complexes from transfected tumor cells, and the fusion of the KDEL-deleted gp96 with murine IgG1 facilitated its detection by ELISA and FACS analysis and its purification by affinity chromatography with the aid of Protein A.

4.3.5.1 Expression Systems

Nucleotide sequences encoding an HSP or α2M molecule can be inserted into the expression vector for propagation and expression in recombinant cells. An expression construct, as used herein, refers to a nucleotide sequence encoding an HSP or α2M operably associated with one or more regulatory regions which allows expression of the HSP or α2M molecule in an appropriate host cell. "Operably-associated" refers to an association in which the regulatory regions and the HSP or α2M polypeptide sequence to be expressed are joined and positioned in such a way as to permit transcription, and ultimately, translation of the HSP or α2M sequence. A variety of expression vectors may be used for the expression of HSPs or α2M, including, but not limited to, plasmids, cosmids, phage, phagemids, or modified viruses. Examples include bacteriophages such as lambda derivatives, or plasmids such as pBR322 or pUC plasmid derivatives or the Bluescript vector (Stratagene). Typically, such expression vectors comprise a functional origin of replication for propagation of the vector in an appropriate host cell, one or more restriction endonuclease sites for insertion of the HSP or α2M gene sequence, and one or more selection markers.

For expression of HSPs or α2M in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), the β-interferon gene, and the HSP70 gene (Williams et al., 1989, Cancer Res. 49: 2735-42; Taylor et al., 1990, Mol. Cell. Biol. 10: 165-75). The efficiency of expression of the HSP or α2M in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153: 516-544; Gorman, 1990, Curr. Op. in Biotechnol. 1: 36-47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors that can be replicated and maintained in at least two types of host cells.

In addition, the expression vector may contain selectable or screenable marker genes for initially isolating or identifying host cells that contain DNA encoding an HSP or α2M. For long term, high yield production of HSPs or α2M, stable expression in mammalian cells is preferred. A number of selection systems may be used for mammalian cells, including, but not limited, to the Herpes simplex virus thymidine kinase (Wigler et al., 1977, Cell 11: 223), hypoxanthine-guanine phosphoribosyltransferase (Szybalski and Szybalski, 1962, Proc. Natl. Acad. Sci. U.S.A. 48: 2026), and adenine phosphoribosyltransferase (Lowy et al., 1980, Cell 22: 817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler et al., 1980, Natl. Acad. Sci. U.S.A. 77: 3567; O'Hare et al., 1981, Proc. Natl. Acad. Sci. U.S.A. 78: 1527); gpt, which confers resistance to mycophenolic acid (Mulligan and Berg, 1981, Proc. Natl. Acad. Sci. U.S.A. 78: 2072); neomycin phosphotransferase (neo), which confers resistance to the aminoglycoside G-418 (Colberre-Garapin et al., 1981, J. Mol. Biol. 150: 1); and hygromycin phosphotransferase (hyg), which confers resistance to hygromycin (Santerre et al., 1984, Gene 30: 147). Other selectable markers, such as but not limited to histidinol and Zeocin™ can also be used.

The expression construct comprising an HSP- or α2M-coding sequence operably associated with regulatory regions can be directly introduced into appropriate host cells for expression and production of the HSP or α2M complexes of the invention without further cloning (see, for example, U.S. Pat. No. 5,580,859). The expression constructs may also contain DNA sequences that facilitate integration of the coding sequence into the genome of the host cell, e.g., via homologous recombination. In this instance, it is not necessary to employ an expression vector comprising a replication origin suitable for appropriate host cells in order to propagate and express the HSP or α2M molecule in the host cells.

Expression constructs containing cloned HSP or α2M coding sequences can be introduced into the mammalian host cell by a variety of techniques known in the art, including but not limited to calcium phosphate mediated transfection (Wigler et al., 1977, Cell 11: 223-232), liposome-mediated transfection (Schaefer-Ridder et al., 1982, Science 215: 166-168), electroporation (Wolff et al., 1987, Proc. Natl. Acad. Sci. 84: 3344), and microinjection (Cappechi, 1980, Cell 22: 479-488).

Any of the cloning and expression vectors described herein may be synthesized and assembled from known DNA sequences by techniques well known in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Alternatively, number of viral-based expression systems may also be utilized with mammalian cells for recombinant expression of HSPs or α2M. Vectors using DNA virus backbones have been derived from simian virus 40 (SV40) (Hamer et al., 1979, Cell 17: 725), adenovirus (Van Doren et al., 1984, Mol. Cell Biol. 4: 1653), adeno-associated virus (McLaughlin et al., 1988, J. Virol. 62: 1963), and bovine papillomas virus (Zinn et al., 1982, Proc. Natl. Acad. Sci. 79: 4897). In cases where an adenovirus is used as an expression vector, the donor DNA sequence may be ligated to an adenovirus transcription/translation control region, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts (see, e.g., Logan and Shenk, 1984, Proc. Natl. Acad. Sci. U.S.A. 81: 3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in E. coli. Following construction and amplification in bacteria, the expression gene construct is transfected into cultured mammalian cells, for example, by the techniques of calcium phosphate coprecipitation or electroporation. For those host cells that do not manifest a transformed phenotype, selection of transformants is achieved by use of a dominant selectable marker, such as histidinol and G418 resistance. For example, BPV vectors such as pBCMGSNeo and pBCMGHis may be used to express HSPs or α2M (Karasuyama et al., Eur. J. Immunol. 18: 97-104; Ohe et al., Human Gene Therapy 6: 325-33) which may then be transfected into a diverse range of cell types for HSP or α2M expression.

Alternatively, the vaccinia 7.5 K promoter may be used (see, e.g., Mackett et al., 1982, Proc. Natl. Acad. Sci. U.S.A. 79: 7415-7419; Mackett et al., 1984, J. Virol. 49: 857-864; Panicali et al., 1982, Proc. Natl. Acad. Sci. U.S.A. 79: 4927-4931) In cases where a human host cell is used, vectors based on the Epstein-Barr virus (EBV) origin (OriP) and EBV nuclear antigen 1 (EBNA-1; a trans-acting replication factor) may be used. Such vectors can be used with a broad range of human host cells, e.g., EBO-pCD (Spickofsky et al., 1990, DNA Prot. Eng. Tech. 2: 14-18), pDR2 and λDR2 (available from Clontech Laboratories).

Recombinant HSP or α2M expression can also be achieved by a retrovirus-based expression system. In contrast to transfection, retroviruses can efficiently infect and transfer genes to a wide range of cell types including, for example, primary hematopoietic cells. In retroviruses such as Moloney murine leukemia virus, most of the viral gene sequences can be removed and replaced with an HSP or α2M coding sequence, while the missing viral functions can be supplied in trans. The host range for infection by a retroviral vector can also be manipulated by the choice of envelope used for vector packaging.

For example, a retroviral vector can comprise a 5' long terminal repeat (LTR), a 3' LTR, a packaging signal, a bacterial origin of replication, and a selectable marker. The ND-associated antigenic peptide DNA is inserted into a position between the 5' LTR and 3' LTR, such that transcription from the 5' LTR promoter transcribes the cloned DNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells (see McLauchlin et al., 1990, Prog. Nucleic Acid Res. and Molec. Biol. 38: 91-135; Morgenstern et al., 1990, Nucleic Acid Res. 18: 3587-3596; Choulika et al., 1996, J. Virol 70: 1792-1798; Boesen et al., 1994, Biotherapy 6: 291-302; Salmons and Gunzberg, 1993, Human Gene Therapy 4: 129-141; and Grossman and Wilson, 1993, Curr. Opin. in Genetics and Devel. 3: 110-114).

The recombinant cells may be cultured under standard conditions of temperature, incubation time, optical density, and media composition. Alternatively, cells may be cultured under conditions emulating the nutritional and physiological requirements of a cell in which the HSP is endogenously expressed. Modified culture conditions and media may be used to enhance production of HSP-peptide complexes. For example, recombinant cells may be grown under conditions that promote inducible HSP expression.

Alpha-2-macroglobulin and HSP polypeptides of the invention may be expressed as fusion proteins to facilitate recovery and purification from the cells in which they are expressed. For example, an HSP or α2M polypeptide may contain a signal sequence leader peptide to direct its translocation across the ER membrane for secretion into culture medium. Further, an HSP or α2M polypeptide may contain an affinity label, such as a affinity label, fused to any portion of the HSP or α2M polypeptide not involved in binding antigenic peptide, such as for example, the carboxyl terminal. The affinity label can be used to facilitate purification of the protein, by binding to an affinity partner molecule.

Various methods for production of such fusion proteins are well known in the art. The manipulations which result in their production can occur at the gene or protein level, preferably at the gene level. For example, the cloned coding region of an HSP or α2M polypeptide may be modified by any of numerous recombinant DNA methods known in the art (Sambrook et al., 1990, Molecular Cloning, A Laboratory Manual, 2d ed., Cold Spring Harbor Laboratory, Cold Spring Harbor, N.Y.; Ausubel et al., in Chapter 8 of Current Protocols in Molecular Biology, Greene Publishing Associates and Wiley Interscience, New York). It will be apparent from the following discussion that substitutions, deletions, insertions, or any combination thereof are introduced or combined to arrive at a final nucleotide sequence encoding an HSP or α2M polypeptide.

In various embodiments, fusion proteins comprising the HSP or α2M polypeptide may be made using recombinant DNA techniques. For example, a recombinant gene encoding an HSP or α2M polypeptide may be constructed by introducing an HSP or α2M gene fragment in the proper reading frame into a vector containing the sequence of an affinity label, such that the HSP or α2M polypeptide is expressed as a peptide-tagged fusion protein. Affinity labels, which may be recognized by specific binding partners, may be used for affinity purification of the HSP or α2M polypeptide.

In a preferred embodiment, the affinity label is fused at its amino terminal to the carboxyl terminal of HSP or α2M. The precise site at which the fusion is made in the carboxyl terminal is not critical. The optimal site can be determined by routine experimentation.

A variety of affinity labels known in the art may be used, such as, but not limited to, the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the *E. coli* maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Other affinity labels may impart fluorescent properties to an HSP or α2M polypeptide, e.g., portions of green fluorescent protein and the like. Other possible affinity labels are short amino acid sequences to which monoclonal antibodies are available, such as but not limited to the following well known examples, the FLAG epitope, the myc epitope at amino acids 408-439, the influenza virus hemagglutinin (HA) epitope. Other affinity labels are recognized by specific binding partners and thus facilitate isolation by affinity binding to the binding partner which can be immobilized onto a solid support. Some affinity labels may afford the HSP or α2M polypeptide novel structural properties, such as the ability to form multimers. Dimerization of an HSP or α2M polypeptide with a bound peptide may increase avidity of interaction between the HSP or α2M polypeptide and its partner in the course of antigen presentation. These affinity labels are usually derived from proteins that normally exist as homopolymers. Affinity labels such as the extracellular domains of CD8 (Shiue et al., 1988, J. Exp. Med. 168:1993-2005), or CD28 (Lee et al., 1990, J. Immunol. 145:344-352), or portions of the immunoglobulin molecule containing sites for interchain disulfide bonds, could lead to the formation of multimers. As will be appreciated by those skilled in the art, many methods can be used to obtain the coding region of the above-mentioned affinity labels, including but not limited to, DNA cloning, DNA amplification, and synthetic methods. Some of the affinity labels and reagents for their detection and isolation are available commercially.

A preferred affinity label is a non-variable portion of the immunoglobulin molecule. Typically, such portions comprise at least a functionally operative CH2 and CH3 domain of the constant region of an immunoglobulin heavy chain. Fusions are also made using the carboxyl terminus of the Fc portion of a constant domain, or a region immediately amino-terminal to the CHI of the heavy or light chain. Suitable immunoglobulin-based affinity label may be obtained from IgG-1, -2, -3, or -4 subtypes, IgA, IgE, IgD, or IgM, but preferably IgG1. Preferably, a human immunoglobulin is used when the HSP or α2M polypeptide is intended for in vivo use for humans. Many DNA encoding immunoglobulin light or heavy chain constant regions is known or readily available from cDNA libraries. See, for example, Adams et al., Biochemistry, 1980, 19:2711-2719; Gough et al., 1980, Biochemistry, 19:2702-2710; Dolby et al., 1980, Proc. Natl. Acad. Sci. U.S.A., 77:6027-6031; Rice et al., 1982, Proc. Natl. Acad. Sci. U.S.A., 79:7862-7865; Falkner et al., 1982, Nature, 298:286-288; and Morrison et al., 1984, Ann. Rev. Immunol, 2:239-256. Because many immunological reagents and labeling systems are available for the detection of immunoglobulins, the HSP or α2M polypeptide-Ig fusion protein can readily be detected and quantified by a variety of immunological techniques known in the art, such as the use of enzyme-linked immunosorbent assay (ELISA), immunoprecipitation, fluorescence activated cell sorting (FACS), etc. Similarly, if the affinity label is an epitope with readily available antibodies, such reagents can be used with the techniques mentioned above to detect, quantitate, and isolate the HSP or α2M polypeptide containing the affinity label. In many instances, there is no need to develop specific antibodies to the HSP or α2M polypeptide.

A particularly preferred embodiment is a fusion of an HSP or α2M polypeptide to the hinge, the CH2 and CH3 domains of human immunoglobulin G-1 (IgG-1; see Bowen et al., 1996, J. Immunol. 156:442-49). This hinge region contains three cysteine residues which are normally involved in disulfide bonding with other cysteines in the Ig molecule. Since none of the cysteines are required for the peptide to function as a tag, one or more of these cysteine residues may optionally be substituted by another amino acid residue, such as for example, serine.

Various leader sequences known in the art can be used for the efficient secretion of HSP or α2M polypeptide from bacterial and mammalian cells (von Heijne, 1985, J. Mol. Biol. 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981, Proc. Natl. Acad. Sci. 78:5812-5816). Preferred leader sequences for targeting HSP or α2M polypeptide expression in bacterial cells include, but are not limited to, the leader sequences of the *E. coli* proteins OmpA (Hobom et al., 1995, Dev. Biol. Stand. 84:255-262), Pho A (Oka et al., 1985, Proc. Natl. Acad. Sci 82:7212-16), OmpT (Johnson et al., 1996, Protein Expression 7:104-113), LamB and OmpF (Hoffman & Wright, 1985, Proc. Natl. Acad. Sci. USA 82:5107-5111), β-lactamase (Kadonaga et al., 1984, J. Biol. Chem. 259:2149-54), enterotoxins (Morioka-Fujimoto et al., 1991, J. Biol. Chem. 266:1728-32), and the *Staphylococcus aureus* protein A (Abrahmsen et al., 1986, Nucleic Acids Res. 14:7487-7500), and the *B. subtilis* endoglucanase (Lo et al., Appl. Environ. Microbiol. 54:2287-2292), as well as artificial and synthetic signal sequences (MacIntyre et al., 1990, Mol. Gen. Genet. 221:466-74; Kaiser et al., 1987, Science, 235: 312-317).

DNA sequences encoding a desired affinity label or leader peptide, which may be readily obtained from libraries, produced synthetically, or may be available from commercial suppliers, are suitable for the practice of this invention. Such methods are well known in the art.

4.4. Complexing Proteins and Peptides to HSP and α2M

Described herein are exemplary methods for complexing in vitro the HSP or α2M with a population of proteins and/or peptides which have been prepared from antigenic cells, a cellular fraction thereof, or viral particles. The population of proteins and/or peptides are from a protein preparation of the antigenic cells as described in Section 4.2.1. In certain embodiments, the peptides are the result of digestion of a protein preparation of antigenic cells, a cellular fraction thereof, or viral particles. The complexing reaction can result in the formation of a covalent bond between a HSP and a protein or peptide of the antigenic cell or viral particle. The complexing reaction can result in the formation of a covalent bond between a α2M and a protein or peptide of the antigenic cell or viral particle. The complexing reaction can also result in the formation of a non-covalent association between a HSP and a protein and/or a peptide, or a α2M and a protein and/or a peptide.

Prior to complexing, the HSPs can be pretreated with ATP or exposed to acidic conditions to remove any peptides that may be non-covalently associated with the HSP of interest. When the ATP procedure is used, excess ATP is removed from the preparation by the addition of apyranase as described by Levy, et al., 1991, *Cell* 67:265-274. When acidic conditions are used, the buffer is readjusted to neutral pH by the addition of pH modifying reagents. A preferred, exemplary protocol for the noncovalent complexing of a population of peptides (average length between 7 to 20 amino acids) to an HSP or α2M in vitro is discussed below:

The population of peptides (1 µg) and the pretreated HSP (9 µg) are admixed to give an approximately 5 peptides (or proteins): 1 HSP molar ratio. Then, the mixture is incubated for 15 minutes to 3 hours at 4° to 45° C. in a suitable binding buffer such as one containing 20 mM sodium phosphate, pH 7.2, 350 mM NaCl, 3 mM MgCl$_2$ and 1 mM phenyl methyl sulfonyl fluoride (PMSF). The preparations are centrifuged through a Centricon 10 assembly (Millipore) to remove any unbound peptide. The non-covalent association of the proteins/peptides with the HSPs can be assayed by High Performance Liquid Chromatography (HPLC) or Mass Spectrometry (MS).

In an alternative embodiment of the invention, preferred for producing non-covalent complexes of HSP70 to proteins/peptides, 5-10 micrograms of purified HSP70 is incubated with equimolar quantities of proteins/peptides in 20 mM sodium phosphate buffer pH 7.5, 0.5M NaCl, 3 mM MgCl$_2$ and 1 mM ADP in a volume of 100 microliter at 37° C. for 1 hr. This incubation mixture is centrifuged one or more times if necessary, through a Centricon 10 assembly (Millipore) to remove any unbound peptide.

In an alternative embodiment of the invention, preferred for producing non-covalent complexes of gp96 or HSP90 to peptides, 5-10 micrograms of purified gp96 or HSP90 is incubated with equimolar or excess quantities of the proteins/peptides in a suitable buffer such as one containing 20 mM sodium phosphate buffer pH 7.5, 0.5M NaCl, 3 mM MgCl2 at 60-65° C. for 5-20 min. This incubation mixture is allowed to cool to room temperature and centrifuged one or more times if necessary, through a Centricon 10 assembly (Millipore) to remove any unbound peptide.

Following complexing with antigenic proteins and/or antigenic peptides, an immunogenic HSP complex or α2M complex can optionally be assayed using, for example, the mixed lymphocyte target cell assay (MLTC) described below. Once HSP-peptide complexes and/or HSP-protein complexes have been isolated and diluted, they can be optionally characterized further in animal models using the preferred administration protocols and excipients discussed below.

As an alternative to making non-covalent complexes of HSPs and proteins/peptides, a population of proteins/peptides can be covalently attached to HSPs.

In one embodiment, HSPs are covalently coupled to proteins and/or peptides in a protein preparation by chemical crosslinking. Chemical crosslinking methods are well known in the art. For example, in a preferred embodiment, glutaraldehyde crosslinking may be used. Glutaradehyde crosslinking has been used for formation of covalent complexes of peptides and HSPs (see Barrios et al., 1992, Eur. J. Immunol. 22: 1365-1372). Preferably, 1-2 mg of HSP-peptide complex is crosslinked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302). Alternatively, a HSP and a population of protein/peptides can be crosslinked by ultraviolet (UV) crosslinking under conditions known in the art.

In another embodiment of the invention, a population of proteins and/or peptides in a protein preparation can be non-covalently complexed to α2M by incubating the proteins/peptides with α2M at a 50:1 molar ratio and incubated at 50° C. for 10 minutes followed by a 30 minute incubation at 25° C. Free (uncomplexed) peptides can be removed by size exclusion filters. Complexes are preferably measured by a scintillation counter to make sure that on a per molar basis, each HSP or α2M is observed to bind equivalent amounts of proteins/peptide (approximately 0.1% of the starting amount of the peptide). For details, see Binder, 2001, J. Immunol. 166(8):4968-72, which is incorporated herein by reference in its entirety. To reduce the propensity of forming covalent complexes of α2M and the proteins and peptides in these reactions, it will be desirable to inhibit or remove protease activity prior to complexing. This can be accomplished with the use of protease inhibitors, for example, by the methods described in section 4.2.1. Also desirable is adding a reducing agent (such as 2-mercaptoethanol) to the reactions to neutralize nucleophilic compounds present in the protein preparation which may activate α2M for covalent association.

In yet another embodiment, a population of antigenic proteins and/or antigenic peptides in a protein preparation can be complexed to α2M covalently by methods as described in PCT publications WO 94/14976 and WO 99/50303 for complexing a peptide to α2M, which are incorporated herein by reference in their entirety. For example, antigenic proteins and/or antigenic peptides can be incorporated into α2M by ammonia or methylamine (or other small amine nucleophiles such as ethylamine) during reversal of the nucleophilic activation, employing heat (Grøn and Pizzo, 1998, Biochemistry, 37: 6009-6014; which is incorporated herein by reference in its entirety). Such conditions that allow fortuitous trapping of peptides by α2M can be employed to prepare the α2M complexes of the invention. Covalent linking of a population of antigenic proteins/peptides to α2M can also be performed using a bifunctional crosslinking agent. Such crosslinking agents and methods of their use are also well known in the art. Preferably, the crosslinking agent is inactivated and/or removed after the complexes are formed.

In yet another embodiment, a population of proteins/peptides can be complexed to a mixture of HSP and α2M in the same reaction by the non-covalent or covalent methods described above.

Complexes of HSP and antigenic proteins and/or peptides from separate covalent and/or non-covalent complexing reactions can optionally be combined to form a composition before administration to a subject. Complexes of α2M and antigenic proteins and/or peptides from separate covalent and/or non-covalent complexing reactions can also optionally be combined to form a composition before administration to a subject.

4.5. Prevention and Treatment of Cancer and Infectious Diseases

In accordance with the invention, a composition of the invention, which comprises complexes of antigenic peptides derived from digested cytosolic and/or membrane-derived proteins of antigenic cells or viral particle and a HSP and/or α2M, is administered to a subject with cancer or an infectious disease. In one embodiment, "treatment" or "treating" refers to an amelioration of cancer or an infectious disease, or at least one discernible symptom thereof. In another embodiment, "treatment" or "treating" refers to an amelioration of at least one measurable physical parameter associated with cancer or an infectious disease, not necessarily discernible by the subject. In yet another embodiment, "treatment" or "treating" refers to inhibiting the progression of a cancer or an infectious disease, either physically, e.g., stabilization of a discernible symptom, physiologically, e.g., stabilization of a physical parameter, or both.

In certain embodiments, the compositions of the present invention are administered to a subject as a preventative measure against such cancer or an infectious disease. As used herein, "prevention" or "preventing" refers to a reduction of the risk of acquiring a given cancer or infectious disease. In one mode of the embodiment, the compositions of the present invention are administered as a preventative measure to a subject having a genetic predisposition to a cancer. In another mode of the embodiment, the compositions of the present invention are administered as a preventative measure to a subject facing exposure to carcinogens including but not limited to chemicals and/or radiation, or to a subject facing exposure to an agent of an infectious disease.

Human subjects are preferred in the therapeutic and prophylactic methods of the invention.

The compositions prepared by methods of the invention comprise complexes of heat shock protein(s) with a population of antigenic peptides, and/or complexes of alpha-2-macroglobulin with a population of antigenic peptides. The compositions appear to induce an inflammatory reaction at the tumor site and can ultimately cause a regression of the tumor burden in the cancer patients treated. The compositions prepared by the methods of the invention can enhance the immunocompetence of the subject and elicit specific immunity against infectious agents or specific immunity against preneoplastic and neoplastic cells. These compositions have the capacity to prevent the onset and progression of infectious diseases, and to inhibit the growth and progression of tumor cells.

The therapeutic regimens and pharmaceutical compositions of the invention that comprise complexes of cytosolic and membrane-derived proteins, may be used in conjunction with additional immune response enhancers or biological response modifiers including, but not limited to, the cytokines IFN-α, IFN-γ, IL-2, IL-4, IL-6, TNF, or other cytokine affecting immune cells, as well as complexes of heat shock proteins and antigenic molecules. Furthermore, the compositions of the present invention may be administered either with, or in a preferred embodiment, without an adjuvant.

4.5.1. Target Infectious Diseases

Infectious diseases that can be treated or prevented by the methods of the present invention are caused by infectious agents including, but not limited to, viruses, bacteria, fungi protozoa and parasites. The invention is not limited to treating or preventing infectious diseases caused by intracellular pathogens.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), nnderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, bacteria that have an intracellular stage in its life cycle, mycobacteria, *rickettsia*, mycoplasma, *neisseria* and legionella.

Protozoal diseases that can be treated or prevented by the methods of the present invention are caused by protozoa including, but not limited to, *leishmania,* kokzidioa, and *trypanosoma.*

Parasitic diseases that can be treated or prevented by the methods of the present invention are caused by parasites including, but not limited to, *chlamydia* and *rickettsia*.

4.5.2. Target Cancers

Types of cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In a specific embodiment, the cancer is metastatic. In another specific embodiment, the patient having a cancer is immunosuppressed by reason of having undergone anti-cancer therapy (e.g., chemotherapy radiation) prior to administration of the HSP and/or α2M-peptide complexes or administration of the HSP- and/or α2M-sensitized APC.

There are many reasons why immunotherapy as provided by the present invention is desired for use in cancer patients. First, if cancer patients are immunosuppressed, surgery with anesthesia and subsequent chemotherapy may worsen the immunosuppression. With appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

The preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication. The methods of the invention can also be used in individuals at enhanced risk of a particular type of cancer, e.g., due to familial history or environmental risk factors.

4.5.3. Autologous Embodiment

The specific immunogenicity of HSPs and α2M derives not from HSPs or α2M per se, but from the antigenic peptides bound to them. In a preferred embodiment of the invention, the complexes in the compositions of the inventions for use as cancer vaccines are autologous complexes, thereby circumventing two of the most intractable hurdles to cancer immunotherapy. First is the possibility that human cancers, like cancers of experimental animals, are antigenically distinct. To circumvent this hurdle, in a preferred embodiment of the present invention, the HSPs and/or α2M are complexed to antigenic proteins and peptides, and the complexes are used to treat the cancers in the same subject from which the proteins or peptides are derived. Second, most current approaches to cancer immunotherapy focus on determining the CTL-recognized epitopes of cancer cell lines. This approach requires the availability of cell lines and CTLs against cancers. These reagents are unavailable for an overwhelming proportion of human cancers. In an embodiment of the present invention directed to the use of autologous antigenic peptides, cancer immunotherapy does not depend on the availability of cell lines or CTLs nor does it require definition of the antigenic epitopes of cancer cells. These advantages make complexes of HSPs and/or α2M bound to autologous antigenic peptides attractive immunogens against cancer.

In other embodiments, the antigenic peptides in the therapeutic or prophylactic complexes can be prepared from cancerous tissue of the same type of cancer from a subject allogeneic to the subject to whom the complexes are administered.

4.6. Adoptive Immunotherapy

Adoptive immunotherapy refers to a therapeutic approach for treating cancer or infectious diseases in which immune cells are administered to a host with the aim that the cells mediate either directly or indirectly specific immunity to tumor cells and/or antigenic components or regression of the tumor or treatment of infectious diseases, as the case may be. (See e.g., U.S. Pat. No. 5,985,270, issued Nov. 16, 1999, which is incorporated by reference herein in its entirety).

In one embodiment, antigen presenting cells (APC) for use in adoptive immunotherapy are sensitized with HSPs and/or α2M complexed with antigenic proteins and peptides prepared in accordance with the methods described herein. The complexes can be produced by complexing heat shock protein or alpha-2-macroglobulin to antigenic proteins that are derived from at least 50% of the different proteins or at least 100 different proteins present in antigenic cells or viral particles that express an antigenic determinant of an agent that causes the infectious disease. The complexes can also be produced by (a) subjecting a protein preparation derived from cells of said type of cancer to either digestion with a protease or contact with ATP, guanidium hydrochloride, and/or acid, to generate a population of antigenic peptides, and (b) complexing the population of antigenic peptides to heat shock protein or alpha-2-macroglobulin.

In another embodiment, therapy by administration of in vitro complexed antigenic peptides and HSPs and/or α2M prepared by the methods of the invention may be combined with adoptive immunotherapy using APC sensitized by HSP- and/or α2M-antigenic peptide complexes prepared by any method known in the art (see e.g., U.S. Pat. No. 5,985,270) in which the antigenic peptides display the desired antigenicity (e.g., of the type of cancer or pathogen). The sensitized APC can be administered alone, in combination with the in vitro complexed proteins/peptides and HSPs and/or α2M, or before or after administration of the complexed proteins/peptides and HSPs and/or α2M. In particular, the use of sensitized APC to prevent and treat cancer can further comprise administering to the subject an amount, effective for said treatment or prevention, of complexes comprising heat shock protein and/or alpha-2-macroglobulin, complexed to antigenic proteins/peptides, wherein said complexes were produced as described above. Similarly, the use of sensitized APC in treating or preventing a type of infectious disease, can further comprise administering to the subject an amount, effective for said treatment or prevention, of complexes comprising heat shock protein and/or alpha-2-macroglobulin, complexed to antigenic proteins/peptides.

Furthermore, the mode of administration of the in vitro complexed antigenic proteins/peptides and HSPs and/or α2M can be varied, including but not limited to, e.g., subcutaneously, intravenously or intramuscularly, although intradermally is preferred. In another specific embodiment, adoptive immunotherapy by administration of the antigen presenting cells sensitized with complexes made according to the present invention can be combined with therapy by administration by HSP- and/or α2M-antigenic molecule (e.g., peptide) complexes prepared by any method known in the art (see e.g., U.S. Pat. Nos. 5,750,119, 5,837,251, 5,961,979, 5,935,576, PCT publications WO 94/14976 or WO 99/50303) in which the antigenic molecules display the desired antigenicity (e.g., of the type of cancer or pathogen).

4.6.1. Obtaining Antigen-Presenting Cells

The antigen-presenting cells, including but not limited to macrophages, dendritic cells and B-cells, are preferably obtained by production in vitro from stem and progenitor cells from human peripheral blood or bone marrow as described by Inaba, K., et al., 1992, J. Exp. Med. 176:1693-1702. Dendritic cells can be obtained by any of various methods known in the art. By way of example but not limitation, dendritic cells can be obtained by the methods described in Sallusto et al., 1994, J Exp Med 179:1109-1118 and Caux et al., 1992, Nature 360, 258-261 which are incorporated herein by reference in their entireties. In a preferred aspect, human dendritic cells obtained from human blood cells are used.

APC can be obtained by any of various methods known in the art. In one aspect, human macrophages are used, obtained from human blood cells. By way of example but not limitation, macrophages can be obtained as follows:

Mononuclear cells are isolated from peripheral blood of a patient (preferably the patient to be treated), by Ficoll-Hypaque gradient centrifugation and are seeded on tissue culture dishes which are pre-coated with the patient's own serum or with other AB+human serum. The cells are incubated at 37° C. for 1 hour, then non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF).

4.6.2. Sensitization of Macrophages and Antigen Presenting Cells with HSP-Peptide or α2M-Peptide Complexes APC are sensitized with HSP or α2M bound to antigenic peptides preferably by incubating the cells in vitro with the complexes. The APC are sensitized with complexes of HSPs or α2M and antigenic molecules by incubating in vitro with the HSP-complex or α2M-complex at 37° C. for 15 minutes to 24 hours. By way of example but not limitation, $4 \times 10^7$ dendritic cells can be incubated with 10 microgram gp96-peptide complexes per ml or 100 microgram HSP90-peptide complexes per ml at 37° C. for 15 minutes-24 hours in 1 ml plain RPMI medium. The cells are washed three times and resuspended in a physiological medium preferably sterile, at a convenient concentration (e.g., $1 \times 10^7$/ml) for injection in a patient. Preferably, the patient into which the sensitized dendritic cells are injected is the patient from which the dendritic cells were originally isolated (autologous embodiment).

Optionally, the ability of sensitized APC to stimulate, for example, the antigen-specific, class I-restricted cytotoxic T-lymphocytes (CTL) can be monitored by their ability to stimulate CTLs to release tumor necrosis factor, and by their ability to act as targets of such CTLs.

4.6.3. Reinfusion of Sensitized APC

The sensitized APCs are reinfused into the patient systemically, preferably intradermally, by conventional clinical procedures. These activated cells are reinfused, preferentially by systemic administration into the autologous patient. Patients generally receive from about $10^6$ to about $10^{12}$ sensitized dendritic cells depending on the condition of the patient. In some regimens, patients may optionally receive in addition a suitable dosage of a biological response modifier including but not limited to the cytokines IFN-α, IFN-γ, IL-2, IL-4, IL-6, TNF or other cytokine growth factor.

4.7. Pharmaceutical Preparations and Methods of Administration

The complexes of antigenic peptides bound to HSPs and/or α2M prepared by the methods of the invention can be administered to a patient at therapeutically effective doses to treat or ameliorate a cell proliferative disorder or infectious disease. A therapeutically effective dose refers to that amount of the complexes sufficient to result in amelioration of symptoms of such a disorder.

4.7.1. Effective Dose

The compositions of the present invention, comprising an immunogenic, effective amount of complexes of a population of antigenic peptides with HSP and/or α2M are administered to a subject in need of treatment against cancer or an infectious disease, as a method of inducing an immune response against that cancer or infectious disease. Toxicity and therapeutic efficacy of such complexes can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Complexes that exhibit large therapeutic indices are preferred. While complexes that exhibit toxic side effects may be used, care should be taken to design a delivery system that targets such complexes to the site of affected tissue in order to minimize potential damage to uninfected cells and, thereby, reduce side effects.

In one embodiment, the data obtained from the cell culture assays and animal studies can be used in formulating a range of dosage for use in humans. The dosage of complexes lies preferably within a range of circulating concentrations that include the $ED_{50}$ with little or no toxicity. The dosage may vary within this range depending upon the dosage form employed and the route of administration utilized. For any complexes used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In another embodiment, an amount of hsp70- and/or gp96-antigenic molecule complexes is administered that is in the range of about 10 microgram to about 600 micrograms for a human patient. The dosage for hsp-90 peptide complexes in a human patient provided by the present invention is in the range of about 50 to 5,000 micrograms, the preferred dosage being 100 micrograms. The doses recited above are preferably given once weekly for a period of about 4-6 weeks, and the mode or site of administration is preferably varied with each administration. Thus, by way of example and not limitation, the first injection may be given subcutaneously on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half on an other site on the same day. Alternatively, the mode of administration is sequentially varied, e.g., weekly injections are given in sequence intradermally, intramuscularly, intravenously or intraperitoneally.

After 4-6 weeks, further injections are preferably given at two-week intervals over a period of time of one month. Later injections may be given monthly. The pace of later injections may be modified, depending upon the patient's clinical progress and responsiveness to the immunotherapy.

In yet another embodiment of the invention, an amount of hsp70- and/or gp96-antigenic peptide complexes is administered that is in the range of about 0.1 micrograms to about 60 micrograms for a human patient. In another specific embodiment, the therapeutically effective amount of hsp70- and/or gp96-antigenic molecule complexes is less than 10 micrograms, e.g., in the range of 0.1 to 9 micrograms; the preferred human dosage being substantially equivalent to the dosage used in a 25 g mouse, e.g., in the range of 0.5 to 2.0 micrograms. The preferred dosage for hsp90-antigenic molecule complexes in a human patient provided by the present invention is in the range of about 5 to 500 micrograms. In a specific embodiment, the therapeutically effective amount of hsp90-antigenic molecule complexes is less than 50 micrograms, e.g., in the range of 5 to 49 micrograms; the preferred dosage being in the range of 5 to 40 micrograms. These doses are preferably administered intradermally or mucosally. By way of example, the doses can be administered, preferably intradermally, every other day for a total of 5 injections. In a preferred embodiment, the doses recited above are given once weekly for a period of about 4 to 6 weeks, and the mode of site of administration is preferably varied with each administration. In a preferred example, intradermal administrations are given, with each site of administration varied sequentially.

Accordingly, the invention provides methods of preventing and treating cancer or an infectious disease in a subject comprising administering a composition which stimulates the immunocompetence of the host individual and elicits specific immunity against the preneoplastic and/or neoplastic cells or infected cells.

4.7.2. Formulations and Use

Pharmaceutical compositions for use in accordance with the present invention may be formulated in conventional manner using one or more physiologically acceptable carriers or excipients.

Thus, the complexes and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active complexes.

For buccal administration the compositions may take the form of tablets or lozenges formulated in conventional manner.

For administration by inhalation, the complexes for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the complexes and a suitable powder base such as lactose or starch.

The complexes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The complexes may also be formulated in rectal compositions such as suppositories or retention enemas, e.g., containing conventional suppository bases such as cocoa butter or other glycerides.

In addition to the formulations described previously, the complexes may also be formulated as a depot preparation. Such long acting formulations may be administered by implantation (for example subcutaneously or intramuscularly) or by intramuscular injection. Thus, for example, the complexes may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

4.7.3. Kits

The invention also provides kits for carrying out the methods and/or therapeutic regimens of the invention. In one embodiment, such kits comprise in one or more containers protein preparations comprising antigenic proteins and peptides for combining with HSPs and/or α2M that are provided in a second container. In another embodiment, such kits comprise in one or more containers digested peptides comprising antigenic peptides for combining with HSPs and/or α2M that are provided in a second container. Alternatively, proteins and/or peptides can be supplied in one or more containers for complexing to HSPs and/or α2M isolated from a specific patient for autologous administration. Optionally, a purified HSP for complexing to proteins and peptides is further provided in a second container.

In another embodiment, such kits comprise in one or more containers therapeutically or prophylactically effective amounts of the complexed proteins/peptides to HSPs and/or α2M, preferably purified, in pharmaceutically acceptable form. The kits optionally further comprise in a second container sensitized APCs, preferably purified.

The HSP or α2M complexes in a container of a kit of the invention may be in the form of a pharmaceutically acceptable solution, e.g., in combination with sterile saline, dextrose solution, or buffered solution, or other pharmaceutically acceptable sterile fluid. Alternatively, the HSP and α2M complexes may be lyophilized or desiccated; in this instance, the kit optionally further comprises in a container a pharmaceutically acceptable solution (e.g., saline, dextrose solution, etc.), preferably sterile, to reconstitute the HSPs and α2M or α2M and HSP-containing complexes to form a solution for injection purposes.

In another embodiment, a kit of the invention further comprises a needle or syringe, preferably packaged in sterile form, for injecting the HSP and α2M complex, and/or a packaged alcohol pad. Instructions are optionally included for administration of α2M and HSP-peptide complexes by a clinician or by the patient.

4.8. Determination of Immunogenicity of the HSP and α2M Complexes

Optionally, the HSP-protein complexes, HSP-peptide complexes, α2M-protein complexes and α2M-peptide complexes of the invention can be assayed for immunogenicity using any method known in the art. By way of example but not limitation, one of the following procedures can be used. In a preferred embodiment, the ELISPOT assay is used (see, infra, Section 4.9.4).

4.8.1. The MLTC Assay

Briefly, mice are injected with an amount of the HSP- and/or α2M complexes, using any convenient route of administration. As a negative control, other mice are injected with, e.g., HSP complexed to proteins and/or peptides prepared from normal tissue. Cells known to contain specific antigens, e.g. tumor cells or cells infected with an agent of an infectious disease, may act as a positive control for the assay. The mice are injected twice, 7-10 days apart. Ten days after the last immunization, the spleens are removed and the lymphocytes released. The released lymphocytes may be re-stimulated subsequently in vitro by the addition of dead cells that expressed the antigen of interest.

For example, $8 \times 10^6$ immune spleen cells may be stimulated with $4 \times 10^4$ mitomycin C treated or γ-irradiated (5-10, 000 rads) cells containing the antigen of interest (or cells transfected with an appropriate gene, as the case may be) in 3 ml RPMI medium containing 10% fetal calf serum. In certain cases 33% secondary mixed lymphocyte culture supernatant may be included in the culture medium as a source of T cell growth factors (See, Glasebrook, et al., 1980, *J. Exp. Med.* 151:876). To test the primary cytotoxic T cell response after immunization, spleen cells may be cultured without stimulation. In some experiments spleen cells of the immunized mice may also be re-stimulated with antigenically distinct cells, to determine the specificity of the cytotoxic T cell response.

Six days later the cultures are tested for cytotoxicity in a 4 hour $^{51}$Cr-release assay (See, Palladino, et al., 1987, *Cancer Res.* 47:5074-5079 and Blachere, at al., 1993, *J. Immunotherapy* 14:352-356). In this assay, the mixed lymphocyte culture is added to a target cell suspension to give different effector:target (E:T) ratios (usually 1:1 to 40:1). The target cells are prelabelled by incubating $1 \times 10^6$ target cells in culture medium containing 20 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelletted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

4.8.2. CD4+ T-Cell Proliferation Assay

Primary T cells are obtained from spleen, fresh blood, or CSF and purified by centrifugation using FICOLL-PAQUE PLUS (Pharmacia, Upsalla, Sweden) essentially as described by Kruse and Sebald, 1992, EMBO J. 11: 3237-3244. The peripheral blood mononuclear cells are incubated for 7-10 days with a lysate of cells expressing an antigenic molecule. Antigen presenting cells may, optionally be added to the culture 24 to 48 hours prior to the assay, in order to process and present the antigen in the lysate. The cells are then harvested by centrifugation, and washed in RPMI 1640 media (GibcoBRL, Gaithersburg, Md.). $5 \times 10^4$ activated T cells/well are in RPMI 1640 media containing 10% fetal bovine serum, 10 mM HEPES, pH 7.5, 2 mM L-glutamine, 100 units/ml penicillin G, and 100 µg/ml streptomycin sulphate in 96 well plates for 72 hrs at 37° C., pulsed with 1 µCi $^3$H-thymidine (DuPont NEN, Boston, Mass.)/well for 6 hrs, harvested, and radioactivity measured in a TOPCOUNT scintillation counter (Packard Instrument Co., Meriden, Conn.).

4.8.3. Antibody Response Assay

In a certain embodiment of the invention, the immunogenicity of an HSP- or α2M-complex is determined by measuring antibodies produced in response to the vaccination with the complex. In one mode of the embodiment, microtitre plates (96-well Immuno Plate II, Nunc) are coated with 50 µl/well of a 0.75 µg/ml solution of a purified, non-HSP- or α2M-complexed form of the proteins/peptides used in the vaccine in PBS at 4° C. for 16 hours and at 20° C. for 1 hour. The wells are emptied and blocked with 200 µl PBS-T-BSA (PBS containing 0.05% (v/v) TWEEN 20 and 1% (w/v) bovine serum albumin) per well at 20° C. for 1 hour, then washed 3 times with PBS-T. Fifty µl/well of plasma or CSF from a vaccinated animal (such as a model mouse or a human patient) is applied at 20° C. for 1 hour, and the plates are washed 3 times with PBS-T. The anti-peptide antibody activity is then measured calorimetrically after incubating at 20° C. for 1 hour with 50 µl/well of sheep anti-mouse or anti-human immunoglobulin, as appropriate, conjugated with horseradish peroxidase (Amersham) diluted 1:1,500 in PBS-T-BSA and (after 3 further PBS-T washes as above) with 50 µl of an o-phenylene diamine (OPD)-$H_2O_2$ substrate solution. The reaction is stopped with 150 µl of 2M $H_2SO_4$ after 5 minutes and absorbance is determined in a Kontron SLT-210 photometer (SLT Lab-instr., Zurich, Switzerland) at 492 nm (ref. 620 nm).

4.8.4. Cytokine Detection Assay

The CD4+T cell proliferative response to HSP- or α2M-complexes of the invention may be measured by detection and quantitation of the levels of specific cytokines. In one embodiment, for example, intracellular cytokines may be measured using an IFN-γ detection assay to test for immunogenicity of a complex of the invention. In an example of this method, peripheral blood mononuclear cells from a subject treated with a HSP-peptide or α2M peptide complex are stimulated with peptide antigens of a given tumor or with peptide antigens of an agent of infectious disease. Cells are then stained with T cell-specific labeled antibodies detectable by flow cytometry, for example FITC-conjugated anti-CD8 and PerCP-labeled anti-CD4 antibodies. After washing, cells are fixed, permeabilized, and reacted with dye-labeled antibodies reactive with human IFN-γ (PE-anti-IFN-γ). Samples are analyzed by flow cytometry using standard techniques.

Alternatively, a filter immunoassay, the enzyme-linked immunospot assay (ELISPOT) assay, may be used to detect specific cytokines surrounding a T cell. In one embodiment, for example, a nitrocellulose-backed microtiter plate is coated with a purified cytokine-specific primary antibody, i.e., anti-IFN-γ, and the plate is blocked to avoid background due to nonspecific binding of other proteins. A sample of mononuclear blood cells, containing cytokine-secreting cells, obtained from a subject treated with a HSP-peptide and/or α2M peptide complex, which sample is diluted onto the wells of the microtitre plate. A labeled, e.g., biotin-labeled, secondary anti-cytokine antibody is added. The antibody cytokine complex can then be detected, i.e. by enzyme-conjugated streptavidin—cytokine-secreting cells will appear as "spots" by visual, microscopic, or electronic detection methods.

4.8.5. Tetramer Assay

In another embodiment, the "tetramer staining" assay (Altman et al., 1996, Science 274: 94-96) may be used to identify antigen-specific T-cells. For example, in one embodiment, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of T cells obtained from a subject treated with a HSP- or α2M-complex. Biotin is then used to stain T cells which express the antigen of interest, i.e., the tumor-specific antigen.

4.9. Monitoring of Effects During Cancer Prevention and Immunotherapy

The effect of immunotherapy with HSP- or α2M-complexes on the development and progression of neoplastic diseases can be monitored by any method known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; and e) changes in levels of putative biomarkers of risk for a particular cancer in individuals at high risk, and f) changes in the morphology of tumors using a sonogram.

The following subsections describe optional, exemplary procedures.

4.9.1. Delayed Hypersensitivity Skin Test

Delayed hypersensitivity skin tests are of great value in the overall immunocompetence and cellular immunity to an antigen. Inability to react to a battery of common skin antigens is termed energy (Sato, T., et al., 1995, *Clin. Immunol. Pathol.* 74:35-43).

Proper technique of skin testing requires that the antigens be stored sterile at 4° C., protected from light and reconstituted shortly before use. A 25- or 27-gauge need ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate test.

4.9.2. Activity of Cytolytic T-Lymphocytes in vitro $8 \times 10^6$ Peripheral blood derived T lymphocytes isolated by the Ficoll-Hypaque centrifugation gradient technique, are restimulated with $4 \times 10^4$ mitomycin C treated tumor cells in 3 ml RPMI medium containing 10% fetal calf serum. In some experiments, 33% secondary mixed lymphocyte culture supernatant or 1L-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxicity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike M., et al., *J. Immunotherapy* 15:165-174).

4.9.3. Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a matter of disease status.

4.9.4. Computed Tomographic (CT) Scan

CT remains the choice of techniques for the accurate staging of cancers. CT has proved more sensitive and specific than any other imaging techniques for the detection of metastases.

4.9.5. Measurement of Putative Biomarkers

The levels of a putative biomarker for risk of a specific cancer are measured to monitor the effect of compositions comprising cytosolic and membrane-derived proteins. For example, in individuals at enhanced risk for prostate cancer, serum prostate-specific antigen (PSA) is measured by the procedure described by Brawer, M. K., et al., 1992, J. Urol. 147:841-845, and Catalona, W. J., et al., 1993, JAMA 270: 948-958; or in individuals at risk for colorectal cancer CEA is measured as described above in Section 4.5.3; and in individuals at enhanced risk for breast cancer, 16-α-hydroxylation of estradiol is measured by the procedure described by Schneider, J. et al., 1982, Proc. Natl. Acad. Sci. ISA 79:3047-3051. The references cited above are incorporated by reference herein in their entirety.

4.9.6. Sonogram

A Sonogram remains an alternative choice of technique for the accurate staging of cancers.

5. EXAMPLE

The following experiment demonstrates that complexes of (a) antigenic peptides derived from a cellular fraction, with (b) either HSP or alpha-2-macroglobulin (α2M), are effective at protecting an animal prophylactically from cancer cell growth.

5.1. Materials and Method

5.1.1 Protein Purification.

For purification of α2M, serum from mice was diluted 1:1 with 0.04M Tris pH 7.6, 0.15M NaCl and applied to a 65 ml Sephacryl S 300R (SIGMA) column equilibrated and eluted with the same buffer. α2M-positive fractions were determined by a dot-blot and the buffer in the fraction was changed to a 0.01M sodium phosphate buffer pH 7.5 by use of a PD-10 column. The protein-containing fractions were applied to a Concanavalin A sepharose column. Bound protein was eluted with 0.2M methylmannose pyranoside and applied to a DEAE column equilibrated with 0.05M sodium acetate buffer. α2M was eluted in a pure form as analyzed by SDS-PAGE and immunoblotting with 0.13M sodium acetate.

In some experiments, α2M was purchased from SIGMA.

Gp96 was obtained by the method described in Section 4.3.3.

5.1.2 Tumor Rejection Assays

All immunizations were done intradermally in 100 μl volume of PBS. Two immunizations were given one week apart. Seven micrograms of α2M or 1 μg of gp96 was used per injection either as a complex or alone. Live tumor cells (100,000) were washed free of culture medium, resuspended in PBS and injected intradermally one week after the last immunization. Tumors were measured in two dimensions. Half of the average was used as the radius of the tumor to calculate the tumor volume. P values were determined using single-classification analysis of variance (ANOVA).

5.1.3 Generation of Complexes.

Cell lysate was obtained from live Meth A cells by dounce homogenization followed by ultracentrifugation. 100,000 g supernatant was treated with 0.1% trifluoroacetic acid (TFA) and 3 mM ATP for 10 hours followed by centrifugation in a CENTRICON membrane filter (Millipore) with a 10 kDa cut off limit. Peptides less than 10 kDa (referred to as "MethA10") were further isolated by binding to a C18 reverse phase column, eluting the peptides with methanol, drying the peptides down in a vacuum, and reconstituting the peptides in a buffer suitable for complexing. Gp96, α2M, or albumin (which was used as a control) was heated to 50° C. in the presence of 50 molar excess of MethA10. The reactions containing the resulting complexes were placed at room temperature for 30 minutes and then placed on ice. Free, uncomplexed peptide was removed using, CENTRICON 50 (Millipore). Complexes thus made were used for immunizations.

5.2. Results

In this experiment, the Meth A tumor model was used to demonstrate the anti-tumor immunity elicited by gp96-peptide complexes, and α2M-peptide complexes. The antigenic MHC I epitopes of this tumor are unknown. Meth A cell lysates were treated with ATP and trifluoroacetic acid (TFA) and the fraction of peptides that were less than 10 kD (MethA10) was collected and complexed to α2M or gp96 as described above. BALB/c mice were immunized with α2M or gp96, un-complexed or complexed with MethA10. BALB/c mice were also immunized with albumin-MethA10 or PBS as negative controls. Immunizations were done twice, one week apart. All mice were challenged intradermally with 100,000 live Meth A cells one week after the last immunization. Tumor growth was monitored every 5 days up to day 20 after the challenge.

TABLE 1

| Compositions used in immunization of mice | Number of mice challenged with tumor cells at day 0 | Number of mice with measurable tumor at day 20 |
|---|---|---|
| MethA10 only | 5 | 5 |
| Albumin-MethA10 | 5 | 5 |
| PBS | 5 | 5 |
| α2M-MethA10 complexes | 5 | 0 |
| Gp96-MethA10 complexes | 5 | 0 |
| Gp96 purified from liver | 5 | 5 |
| α2M purified from serum | 5 | 4 |

The data in Table 1 shows significant tumor protection in mice immunized with α2M-MethA10 ($p<0.05$) or gp96-MethA10 ($p<0.05$) complexes but not mice immunized with α2M alone, gp96 alone, albumin-MethA10 or PBS.

5.3. Discussion

The experiment on immunization against tumors described herein demonstrates a novel approach to immunotherapy of cancers, whereby an array of total cellular peptides from the tumor, including self and antigenic peptides, is complexed to an HSP or α2M. Such complexes effectively stimulated the host's immune system to respond specifically as shown herein. The data indicate that the utility of this approach in prophylaxis can be extended to treatment of pre-existing disease, as well as in treatment and prevention of pathogenic infections.

All references cited herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of preparing complexes of heat shock protein and antigenic peptides, said method comprising the step of complexing a population of antigenic peptides to one or more different heat shock proteins in vitro; wherein the population of antigenic peptides contains at least 50 different peptides and, prior to said complexing step, is produced by a method comprising aliquoting a protein preparation into a plurality of reaction mixtures, wherein each reaction mixture is subjected to (i) digestion with a different protease, or (ii) a different non-enzymatic cleavage method; and pooling the digested or non-enzymatically cleaved reaction mixtures; wherein said protein preparation (a) is from antigenic cells or a cellular fraction thereof, and (b) comprises at least 50% of the different proteins or at least 50 different proteins of said antigenic cells or said cellular fraction.

2. A method of preparing complexes of heat shock protein and antigenic peptides, said method comprising the following steps in the order stated:

(a) aliquoting a protein preparation into a plurality of reaction mixtures, wherein each reaction mixture is subjected to (i) digestion with a different protease, or (ii) a different non-enzymatic cleavage method; and pooling the digested or non-enzymatically cleaved reaction mixtures, to generate a population of antigenic peptides containing at least 50 different peptides, wherein said protein preparation (A) is from antigenic cells or a cellular fraction thereof, and (B) comprises at least 50% of the different proteins or at least 50 different proteins of said antigenic cells or said cellular fraction; and (b) complexing the population of antigenic peptides to one or more different heat shock proteins in vitro.

3. The method of claim 1 or 2, wherein said antigenic cells are cancer cells.

4. The method of claim 1 or 2, wherein the heat shock proteins are purified.

5. The method of claim 1 or 2, wherein the heat shock proteins are selected from the group consisting of HSP 60, HSP70, HSP 90, gp96, calreticulin, grp78, protein disulfide isomerase (PDI), HSP110, and grp170.

6. The method of claim 1 or 2, wherein said antigenic cells are human cancer cells, wherein the heat shock proteins are purified, and wherein the heat shock proteins are selected from the group consisting of HSP 60, HSP70, HSP 90, gp96, calreticulin, grp78, protein disulfide isomerase (PDI), HSP110, and grp170.

7. The method of claim 1 or 2, wherein the heat shock proteins are human heat shock proteins.

8. The method of claim 1 or 2, wherein the heat shock proteins are recombinant heat shock proteins.

9. The method of claim 1 or 2, wherein the heat shock proteins are members of a family of heat shock proteins selected from the group consisting of HSP 60, HSP70, and HSP 90 family.

10. The method of claim 1 or 2, wherein the protein preparation is total cytosolic proteins.

11. The method of claim 1 or 2, wherein the protein preparation is total membrane-bound proteins.

12. The method of claim 1 or 2, wherein the population of antigenic peptides is isolated.

13. The method of claim 1 or 2, wherein said antigenic cells are cancer cells.

14. The method of claim 13, wherein said cancer cells are human cancer cells.

15. The method of claim 14, wherein said heat shock proteins are human heat shock proteins.

16. The method of claim 1 or 2, wherein said antigenic cells are cells that display the antigenicity of an agent that causes an infectious disease.

17. The method of claim 16, wherein said heat shock proteins are human heat shock proteins and said antigenic cells are human antigenic cells.

18. The method of claim 1 or 2, wherein said antigenic cells are cells that are transformed with a nucleic acid molecule encoding an antigen of an infectious agent, which cells express the antigen.

19. The method of claim 1 or 2, wherein said antigenic cells are cells that are transformed with a nucleic acid molecule encoding a tumor-specific antigen or tumor-associated antigen, which cells express the tumor-specific antigen or tumor-associated antigen.

20. The method of claim 1 or 2, wherein said antigenic cells are human antigenic cells.

21. The method of claim 1 or 2, wherein said digestion is carried out under conditions such that the population of antigenic peptides has a size range of from 7 amino acid residues to 20 amino acid residues.

22. The method of claim 1 or 2, further comprising isolating the complexes of heat shock protein and antigenic peptides.

23. The method of claim 1 or 2, wherein said complexing the population of antigenic peptides to the heat shock proteins is via a covalent bond.

24. The method of claim 1 or 2, wherein said complexing the population of antigenic peptides to the heat shock proteins is via a non-covalent bond.

25. The method of claim 1 or 2, wherein the population of antigenic peptides contains at least 100 different peptides.

26. The method of claim 1 or 2, wherein the population of antigenic peptides contains at least 1000 different peptides.

27. The method of claim 1 or 2, wherein the population of antigenic peptides comprises peptides that are in a size range of 8 to 19 amino acid residues.

28. The method of claim 1 or 2, wherein the population of antigenic peptides comprises peptides that are in a size range of at least 20 amino acid residues.

29. The method of claim 1 or 2, wherein said protein preparation is total cellular proteins, total cytosolic proteins, total membrane-bound proteins, or total protein in a cellular fraction, of said antigenic cells, wherein said cellular fraction is selected from the group consisting of a membrane fraction and an organelle fraction.

30. The method of claim 1 or 2, wherein said protein preparation is total protein in an organelle fraction, wherein said organelle fraction is a nuclear fraction, mitochondrial fraction, lysosomal fraction, or endoplasmic reticulum-derived fraction.

31. The method of claim 1 or 2, wherein said heat shock proteins are human heat shock proteins and said antigenic cells are human antigenic cells.

32. The method of claim 31, wherein said protein preparation is total cytosolic proteins.

33. The method of claim 1 or 2, wherein each reaction mixture is subjected to a different non-enzymatic cleavage method.

34. The method of claim 33, wherein cyanogen bromide cleavage is used.

35. The method of claim 33, wherein said antigenic cells are cancer cells.

36. The method of claim 33, wherein the heat shock proteins are purified.

37. The method of claim 33, wherein the heat shock proteins are selected from the group consisting of HSP 60, HSP70, HSP 90, gp96, calreticulin, grp78, protein disulfide isomerase (PDI), HSP110, and grp170.

38. The method of claim 33, wherein said antigenic cells are human cancer cells, wherein the heat shock proteins are purified, and wherein the heat shock proteins are selected from the group consisting of HSP 60, HSP70, HSP 90, gp96, calreticulin, grp78, protein disulfide isomerase (PDI), HSP110, and grp170, and wherein said complexing the population of antigenic peptides to the heat shock proteins is via a non-covalent bond.

39. The method of claim 1 or 2, wherein each reaction mixture is subjected to digestion with a different protease.

40. The method of claim 39, wherein said antigenic cells are cancer cells.

41. The method of claim 39, wherein the heat shock proteins are purified.

42. The method of claim 39, wherein the heat shock proteins are selected from the group consisting of HSP 60, HSP70, HSP 90, gp96, calreticulin, grp78, protein disulfide isomerase (PDI), HSP110, and grp170.

43. The method of claim 39, wherein said complexing the population of antigenic peptides to the heat shock proteins is via a non-covalent bond.

44. The method of claim 39, wherein the population of antigenic peptides contains at least 100 different peptides.

45. The method of claim 39, wherein said protein preparation is total cytosolic proteins.

46. The method of claim 39, wherein said antigenic cells are human cancer cells, wherein the heat shock proteins are purified, and wherein the heat shock proteins are selected from the group consisting of HSP 60, HSP70, HSP 90, gp96, calreticulin, grp78, protein disulfide isomerase (PDI), HSP110, and grp170, and wherein said complexing the population of antigenic peptides to the heat shock proteins is via a non-covalent bond.

* * * * *